United States Patent
Hariri et al.

(10) Patent No.: US 9,575,054 B2
(45) Date of Patent: Feb. 21, 2017

(54) IDENTIFICATION OF ANTITUMOR COMPOUNDS USING PLACENTA

(71) Applicant: Anthrogenesis Corporation, Warren, NJ (US)

(72) Inventors: Robert J. Hariri, Bernardsville, NJ (US); Mohit B. Bhatia, Manalapan, NJ (US); Qian Ye, Livingston, NJ (US)

(73) Assignee: Anthrogenesis Corporation, Warren, NJ (US)

( * ) Notice: Subject to any disclaimer, the term of this patent is extended or adjusted under 35 U.S.C. 154(b) by 4 days.

(21) Appl. No.: 14/380,014

(22) PCT Filed: Feb. 22, 2013

(86) PCT No.: PCT/US2013/027288
§ 371 (c)(1),
(2) Date: Aug. 20, 2014

(87) PCT Pub. No.: WO2013/126674
PCT Pub. Date: Aug. 29, 2013

(65) Prior Publication Data
US 2015/0017663 A1   Jan. 15, 2015

Related U.S. Application Data

(60) Provisional application No. 61/602,524, filed on Feb. 23, 2013.

(51) Int. Cl.
*G01N 33/574* (2006.01)
*G01N 33/50* (2006.01)

(52) U.S. Cl.
CPC ....... *G01N 33/5011* (2013.01); *G01N 33/5088* (2013.01); *G01N 2500/04* (2013.01); *G01N 2500/20* (2013.01)

(58) Field of Classification Search
CPC .................................................... G01N 33/574
USPC ..................................................... 435/7.23, 8
See application file for complete search history.

(56) References Cited

U.S. PATENT DOCUMENTS

| | | | | |
|---|---|---|---|---|
| 2004/0091947 A1* | 5/2004 | Broude | ............. | G01N 33/5017 435/7.23 |
| 2005/0019908 A1* | 1/2005 | Hariri | ..................... | A61M 1/02 435/366 |
| 2010/0255999 A1* | 10/2010 | Mitsiades | ............. | C12M 35/08 506/2 |

* cited by examiner

*Primary Examiner* — Yan Xiao
(74) *Attorney, Agent, or Firm* — Timothy L. Smith; Colin A. Forestal

(57) ABSTRACT

Provided herein are methods of evaluating potential antitumor compounds, and thereby identifying antitumor compounds, using placenta or a portion thereof and tumor cells, and compositions for accomplishing the same. In one embodiment, provided herein is a method of determining whether a potential antitumor compound is effective against a plurality of tumor cells, comprising introducing a plurality of tumor cells to, e.g., into or onto, a mammalian placenta or portion thereof; contacting said plurality of tumor cells for a period of time with said antitumor compound; and determining whether said antitumor compound is effective against said tumor cells, wherein said antitumor compound is effective against said tumor cells if said antitumor compound over said period of time reduces the number of said tumor cells or reduces the growth rate of said tumor cells.

21 Claims, 2 Drawing Sheets

IDENTIFICATION OF ANTITUMOR COMPOUNDS USING PLACENTA

This application is a national stage entry of International Application No. PCT/US2013/027288, filed Feb. 22, 2013, which claims priority to U.S. Provisional Application No. 61/602,524, filed Feb. 23, 2012, the disclosures of which are herein incorporated by reference in their entireties.

1. FIELD

Provided herein are methods of evaluating potential antitumor compounds, and thereby identifying antitumor compounds, using placenta or a portion thereof and tumor cells, and compositions for accomplishing the same.

2. BACKGROUND

Provided herein are methods of evaluating potential antitumor compounds, and thereby identifying antitumor compounds, using placenta or a portion thereof and tumor cells, e.g., to provide a natural environment for tumor cells for a more accurate in vitro evaluation of such compounds.

3. SUMMARY

In one aspect, provided herein are methods of determining the effectiveness of potential anticancer compounds, and thereby identifying antitumor compounds, using a placenta, or a portion thereof (e.g., one or more cotyledons), comprising tumor cells against which the potential anticancer compound is tested. In one embodiment, provided herein is a method of determining whether a potential antitumor compound is effective against a plurality of tumor cells, comprising introducing a plurality of tumor cells to, e.g., into or onto, a mammalian placenta or portion thereof; contacting said plurality of tumor cells for a period of time with said antitumor compound; and determining whether said antitumor compound is effective against said tumor cells, wherein said antitumor compound is effective against said tumor cells if said antitumor compound over said period of time reduces the number of said tumor cells or reduces the growth rate of said tumor cells. In another embodiment, provided herein is a method of determining whether a potential antitumor compound is effective against a plurality of tumor cells, comprising contacting a plurality of tumor cells for a period of time with said antitumor compound; and determining whether said antitumor compound is effective against said tumor cells, wherein said tumor cells are contained or comprised within a placenta or portion thereof, and wherein said antitumor compound is effective against said tumor cells if said antitumor compound over said period of time reduces the number of said tumor cells or reduces the growth rate of said tumor cells. In certain embodiments, at least a plurality of the tumor cells are present in said placenta or portion thereof as three-dimensional aggregates (e.g., one or more cotyledons). In a specific embodiment, the method comprises determining a first number of said tumor cells prior to said contacting, and a second number of said tumor cells after said contacting, wherein if said first number is larger than said first second number, said antitumor compound reduces the number of tumor cells, and said potential antitumor compound is an antitumor compound. In another specific embodiment, the method comprises determining a first number of tumor cells prior to said contacting, and a second number of tumor cells after said contacting; and further determining a control third number of tumor cells at the same time as said second number of tumor cells, wherein said tumor cells in said control have not been contacted with said antitumor compound; wherein if the difference between said second number and said first number is larger than the difference between said third number and said first number, said antitumor compound reduces the growth rate of said tumor cells, and said potential antitumor compound is an antitumor compound.

In certain specific embodiments of the method, said mammalian placenta or portion thereof is a decellularized placenta, e.g., a decellularized placenta or portion thereof comprising a substantially intact vasculature. In certain specific embodiments of the method, said mammalian placenta or portion thereof is a decellularized cotyledon. In other specific embodiments, said mammalian placenta or portion thereof (e.g., cotyledon) is not decellularized, e.g., and comprises a substantially intact vasculature. In certain embodiments, the placenta or portion thereof is partially decellularized.

In certain embodiments of the method, said tumor cells are primary tumor cells. In certain other embodiments, said tumor cells are tumor cell line cells. In other embodiments, the tumor cells are tumor stem cells or cancer stem cells. In specific embodiments, said tumor cells are mesothelioma cells, melanoma cells, adenoma cells, carcinoma cells, adenocarcinoma cells, ductal carcinoma cells, leukemia cells, acute myelogenous leukemia cells, acute myeloid leukemia cells, acute T cell leukemia cells, acute lymphoblastic leukemia cells, hairy cell leukemia cells, acute promyelocytic leukemia cells, lymphoma cells, Burkitt's lymphoma cells, B cell chronic lymphocytic leukemia cells, non-Hodgkin's lymphoma cells, Hodgkin's lymphoma cells, or multiple myeloma cells. rhabdomyosarcoma cells, osteosarcoma cells, neuroblastoma cells, astrocytoma cells, or glioblastoma cells. In more specific embodiments, said tumor cell line is 5637 (Carcinoma), KHOS/NP (Osteosarcoma), MNNG/HOS (Osteosarcoma), Saos-2 (Osteosarcoma), U-2 OS (Osteosarcoma), SJSA-1 (Osteosarcoma), CCF-STTG1 (Astrocytoma), DBTRG-05MG (Glioblastoma), U87 MG (Glioblastoma), T98G (Glioblastoma), SK-N-SH (Neuroblastoma), SK-N-AS (Neuroblastoma), MCF-7 (Adenocarcinoma), MDA-MB-231 (Adenocarcinoma, breast cancer), MDA-MB-436 (Adenocarcinoma), SK-BR-3 (Adenocarcinoma), BT-20 (Carcinoma), BT-474 (Carcinoma), CAMA-1 (Carcinoma), HCC2218 (Carcinoma), SW527 (Carcinoma), MDA-MB-453 (Carcinoma), MDA-MB-435S (Carcinoma), T-47D (Carcinoma), ZR-75-1 (Carcinoma), UACC-812 (Carcinoma), HCC1419 (Carcinoma), HeLa (Adenocarcinoma), Caco-2 (Adenocarcinoma), COLO205 (Adenocarcinoma), COLO320/DM (Adenocarcinoma), DLD-1 (Adenocarcinoma), HCT-15 (Adenocarcinoma), SK-CO-1 (Adenocarcinoma), SW48 (Adenocarcinoma), SW480 (Adenocarcinoma), HCT-8 (Adenocarcinoma), HCT116 (carcinoma, human colorectal cancer), RKO (Carcinoma), LS411N (Carcinoma), T84 (Carcinoma), AGS (Adenocarcinoma), KATO III (Carcinoma), NCI-N87 (Carcinoma), SNU-16 (Carcinoma), 769-P (Adenocarcinoma), 786-0 (Adenocarcinoma), ACHN (Adenocarcinoma), A-498 (Carcinoma), Caki-1 (Carcinoma), G-402 (Leiomyoblastoma), CML-T1 (Leukemia), CTV-1 (Leukemia), JVM-2 (Leukemia), K562 (Leukemia), MHH-CALL2 (Leukemia), NALM-6 (Leukemia), 8E5 (Leukemia), CCRF-SB (Leukemia), CEM/C1 (Leukemia), CEM/C2 (Leukemia), CEM-CM3 (Leukemia), CCRF-HSB-2 (Leukemia), KG-1 (Leukemia), KG-1a (Leukemia), CCRF-CEM (Leukemia), MOLT-3 (Leukemia), SUP-B15 (Leukemia), TALL-104 (Leukemia), Loucy (Leukemia), RS411

(Leukemia), REH (Leukemia), AML-193 (Leukemia), THP-1 (Leukemia), MOLT-3 (Leukemia), Kasumi-1 (Leukemia), Kasumi-3 (Leukemia), BDCM (Leukemia), HL-60 (Leukemia), 12.1 (Leukemia), 19.2 (Leukemia), J.gamma1.WT (Leukemia), J.RT3-T3.5 (Leukemia), P116 (Leukemia), P116.c139 [P116.c39] (Leukemia), D1.1 (Leukemia), J45.01 (Leukemia), MV-4-11 (Leukemia), Kasumi-4 (Leukemia), MEG-01 (Leukemia), KU812 (Leukemia), Mo (Leukemia), JM1 (Leukemia), GDM-1 (Leukemia), CESS (Leukemia), ARH-77 (Leukemia), SK-HEP-1 (Adenocarcinoma), Bel-7402 (Carcinoma), Bel-7404 (Carcinoma), HEP-3B (Carcinoma), HepG2 (Carcinoma), Calu-3 (Adenocarcinoma), NCI-H1395 (Adenocarcinoma), NCI-H1975 (Adenocarcinoma), SK-LU-1 (Adenocarcinoma), NCI-H2122 (Adenocarcinoma), NCI-H727 (Carcinoid), A-427 (Carcinoma), A549 (Carcinoma), SW1573 (Carcinoma), NCI-H358 (Carcinoma), NCI-H460 (Carcinoma), NCI-H292 (Carcinoma), NCI-H82 (Carcinoma), NCI-H226 (Carcinoma), NCI-H526 (Carcinoma), CRL1803-TT (thyroid carcinoma), or MSTO-211H (Mesothelioma).

In certain embodiments of the method, said tumor cells are seeded onto or into said placenta or portion thereof in liquid suspension, e.g., through substantially intact placental vasculature, e.g., substantially intact vascular matrix. In other specific embodiments, the placenta or portion thereof is placed in culture medium comprising tumor cells in liquid suspension, and the tumor cells are allowed to attach to the placenta or portion thereof. In other specific embodiments, the method additionally comprises passaging culture medium through said placenta or portion thereof under conditions such that, in the absence of said antitumor compound, said tumor cells proliferate. In a more specific embodiment, said method additionally comprises passaging culture medium through said placenta or portion thereof under conditions such that, in the absence of said antitumor compound, said tumor cells proliferate, wherein said culture medium is passaged through said substantially intact vasculature.

In certain embodiments, the method additionally comprises introducing a plurality of non-tumor cells to said placenta or portion thereof. In specific embodiments, said non-tumor cells are stromal cells, e.g., bone marrow-derived mesenchymal stromal cells. In certain embodiments, said plurality of non-tumor cells is introduced to said placenta or portion thereof before or after said tumor cells; in other embodiments, said plurality of non-tumor cells is introduced to said placenta or portion thereof at the same time as said tumor cells.

In certain embodiments, e.g., to determine the number or amount of tumor cells, said tumor cells are detectably labeled. Such detectable labels can be, e.g., colorimetric labels, fluorescent labels or radioactive labels. In a specific embodiment, the label is attached to an antibody. Such an antibody can, e.g., bind to a tumor-specific antigen on said tumor cells, or can bind to an antigen specific to said tumor cells. Determining the amount of a label can be used as a proxy for determining the number, or amount, of tumor cells present either or both of before or after contacting with the potential antitumor compound. In a specific embodiment, e.g., where the potential antitumor compound kills tumor cells faster than the tumor cells can proliferate, the difference between said second number of tumor cells and said first number of tumor cells is determined by labeling said tumor cells with a fluorescent antibody; assigning a first fluorescence value to said first number of tumor cells, and a second fluorescence value to said second number of tumor cells; and determining the difference between said second fluorescence value and said first fluorescence value, wherein said difference is correlated to said difference between said second number of tumor cells and said first number of tumor cells. In another embodiment, e.g., said tumor cells are labeled with a fluorescent antibody, and wherein if there is a decrease in fluorescence from said fluorescent antibody after said contacting compared to before said contacting, said potential antitumor compound is an antitumor compound. In another specific embodiment, e.g., wherein the potential antitumor compound slows growth of the tumor cells, the difference between said second number of tumor cells and said first number of tumor cells, and between said third number of tumor cells and said first number of tumor cells, is determined by labeling said tumor cells with a fluorescent antibody; assigning a first fluorescence value to said first number of tumor cells, a second fluorescence value to said second number of tumor cells, and a third fluorescence value to said third number of tumor cells; and determining the difference between said second fluorescence value and said first fluorescence value, wherein said difference is correlated to said difference between said second number of tumor cells and said first number of said tumor cells, and determining the difference between said third fluorescence value and said first fluorescence value, wherein said difference is correlated to said difference between said third number of tumor cells and said first number of tumor cells. In certain embodiments, the tumor cells are labeled with a fluorescent antibody, and wherein if there is a decrease in the rate of increase in fluorescence from said fluorescent antibody over time after said contacting, as compared to a rate of increase in fluorescence from said fluorescent antibody before said contacting, said potential antitumor compound is an antitumor compound.

In other specific embodiments, the number, or amount, of tumor cells present in the assay can be determined using an antigen, e.g., a protein, produced and/or secreted by the tumor cells as a proxy. For example, in a specific embodiment, a number of tumor cells in the method is determined by determining an amount of an antigen produced by said tumor cells. The antigen can be a tumor-specific antigen, or an antigen specific to said tumor cells. In certain specific embodiments, the antigen is not specific to said tumor cells, e.g., the antigen (e.g., protein) is one that known to be generally produced by cells of multiple types. In a specific embodiment of the method, e.g., where the potential anticancer compound kills tumor cells faster than the tumor cells can proliferate, the difference between said second number of tumor cells and said first number of tumor cells is determined by determining a first amount of an antigen produced by said first number of tumor cells prior to said contacting, and a second amount of said antigen produced by said second number of tumor cells after said contacting, and determining the difference between said second amount and said first amount, wherein said difference is correlated to said difference between said second number of tumor cells and said first number of tumor cells. In another specific embodiment, if there is, e.g., a decrease in said antigen after said contacting compared to before said contacting, said potential antitumor compound is an antitumor compound. In another specific embodiment, e.g., in which the potential anticancer compound reduces the growth rate of the tumor cells, the difference between said second number of tumor cells and said first number of tumor cells, and between said third number of tumor cells and said first number of tumor cells, is determined by determining a first amount of an antigen produced by said first number of tumor cells prior to said contacting, and a second amount of said antigen produced by said second number of tumor cells after said contacting, and a third amount of said antigen produced by said third number of tumor cells; and determining the difference between said second amount of antigen and said first amount of antigen, wherein said difference is correlated to said difference between said second number of tumor cells and said first number of said tumor cells, and determining the difference between said third amount of antigen and said first amount of antigen, wherein said difference is correlated to said difference between said third number of tumor cells and said first number of tumor cells. In another specific embodiment, if there is a decrease in the rate of increase in said antigen produced by said tumor cells as compared to a rate of increase in said antigen produced by said tumor cells before said contacting, said potential antitumor compound is an antitumor compound. An exemplary protein that can be used in accordance with these embodiments is calcitonin.

In other embodiments of the method, the tumor cells are genetically modified to express a marker, e.g., a fluorescent protein or luciferase. In a specific embodiment, said fluorescent protein is a green fluorescent protein, e.g., wild-type green fluorescent protein, enhanced green fluorescent protein (eGFP), Emerald™, Superfolder GFP™, Azami Green™, mWasabi™, TagGFP™, TurboGFP™, AcGFP™, ZsGreen™, or T-Sapphire™. In another specific embodiment, said fluorescent protein is a blue fluorescent protein, e.g., enhanced blue fluorescent protein (EBFP), EBFP2™, Azurite™, or mTagBFP™. In another specific embodiment, said fluorescent protein is a cyan fluorescent protein, e.g., enhanced cyan fluorescent protein (ECFP), mECFP™, Cerulean™, mTurquoise™, CyPet™, AmCyan1™, Midori-Ishi Cyan™, TagCFP, or mTFP1 (Teal)™. In another embodiment, said fluorescent protein is a yellow fluorescent protein, e.g., enhanced yellow fluorescent protein (EYFP), Topaz™, Venus™, mCitrine™, YPet™, TagYFP™, PhiYFP™, ZsYellow1™, or mBanana™ In another specific embodiment, said fluorescent protein is an orange fluorescent protein, e.g., Kusabira Orange™, Kusabira Orange2™, mOrange™, mOrange2™, dTomato™, dTomato-Tandem™, TagRFP™, TagRFP-T™, DsRed™, DsRed2™, DsRed-Express™, DsRed-Monomer™, or mTangerine™. In another specific embodiment, said fluorescent protein is a red fluorescent protein, e.g., mRuby™, mApple™, mStrawberry™, AsRed2™, mRFP1™, JRed™ mCherry™, HcRed1™, mRaspberry™, dKeima-Tandem™, HcRed-Tandem™, mPlum™, or AQ143™. In another specific example, said fluorescent protein is a photoactivatable or photoconvertible fluorescent protein, e.g., PA-GFP™ (G), PS-CFP™ (C), PS-CFP (G), PA-mRFP1™ (R), CoralHue Kaede™ (G), CoralHue Kaede™ (R), WtKikGR™ (G), WtKikGR™ (R), mKikGR™ (G), mKikGR™ (R), dEosFP-Tandem™ (G), dEosFP-Tandem™ (R), mEos2FP™ (G), mEos2FP™ (R), Dendra2™ (G), Dendra2™ (R), CoralHue Dronpa™ (G) or Kindling™ (KFP1).

In another specific embodiment, said marker is luciferase.

Where fluorescence, e.g., attributable to a fluorescent protein or luciferase, is used as a proxy, in one embodiment, the difference between said second number of tumor cells and said first number of tumor cells, wherein said tumor cells are engineered to express a fluorescent protein, is determined by assigning a first fluorescence value to said first number of tumor cells, and a second fluorescence value to said second number of tumor cells; and determining the difference between said second fluorescence value and said first fluorescence value, wherein said difference is correlated to said difference between said second number of tumor cells and said first number of tumor cells. In a specific embodiment, said tumor cells are genetically engineered to express a fluorescent protein, and wherein if there is a decrease in fluorescence from said genetically engineered tumor cells after said contacting compared to before said contacting, said potential antitumor compound is an antitumor compound. In another specific embodiment of the method, wherein said tumor cells are engineered to express a fluorescent protein, e.g., where the potential antitumor compound reduces the growth rate of the tumor cells, the difference between said second number of tumor cells and said first number of tumor cells, and between said third number of tumor cells and said first number of tumor cells is determined by assigning a first fluorescence value to said first number of tumor cells, a second fluorescence value to said second number of tumor cells, and a third fluorescence value to said third number of tumor cells; and determining the difference between said second fluorescence value and said first fluorescence value, wherein said difference is correlated to said difference between said second number of tumor cells and said first number of said tumor cells, and determining the difference between said third fluorescence value and said first fluorescence value, wherein said difference is correlated to said difference between said third number of tumor cells and said first number of tumor cells. In another specific embodiment, wherein said tumor cells are genetically engineered to express a fluorescent protein, if there is a decrease in the rate of increase in fluorescence from said genetically engineered tumor cells over time after said contacting, as compared to a rate of increase in fluorescence from said genetically engineered tumor cells before said contacting, said potential antitumor compound is an antitumor compound.

In any of the embodiments disclosed herein, said placenta can be a whole or substantially intact placenta. Where a portion of the placenta is used, said portion of a placenta, in certain embodiments, is shaped to fit a container. Such a container can be, e.g., a tissue culture dish or a well of a multiwall plate.

3.1. BRIEF DESCRIPTION OF DRAWINGS

4. DETAILED DESCRIPTION

Figure 1A:
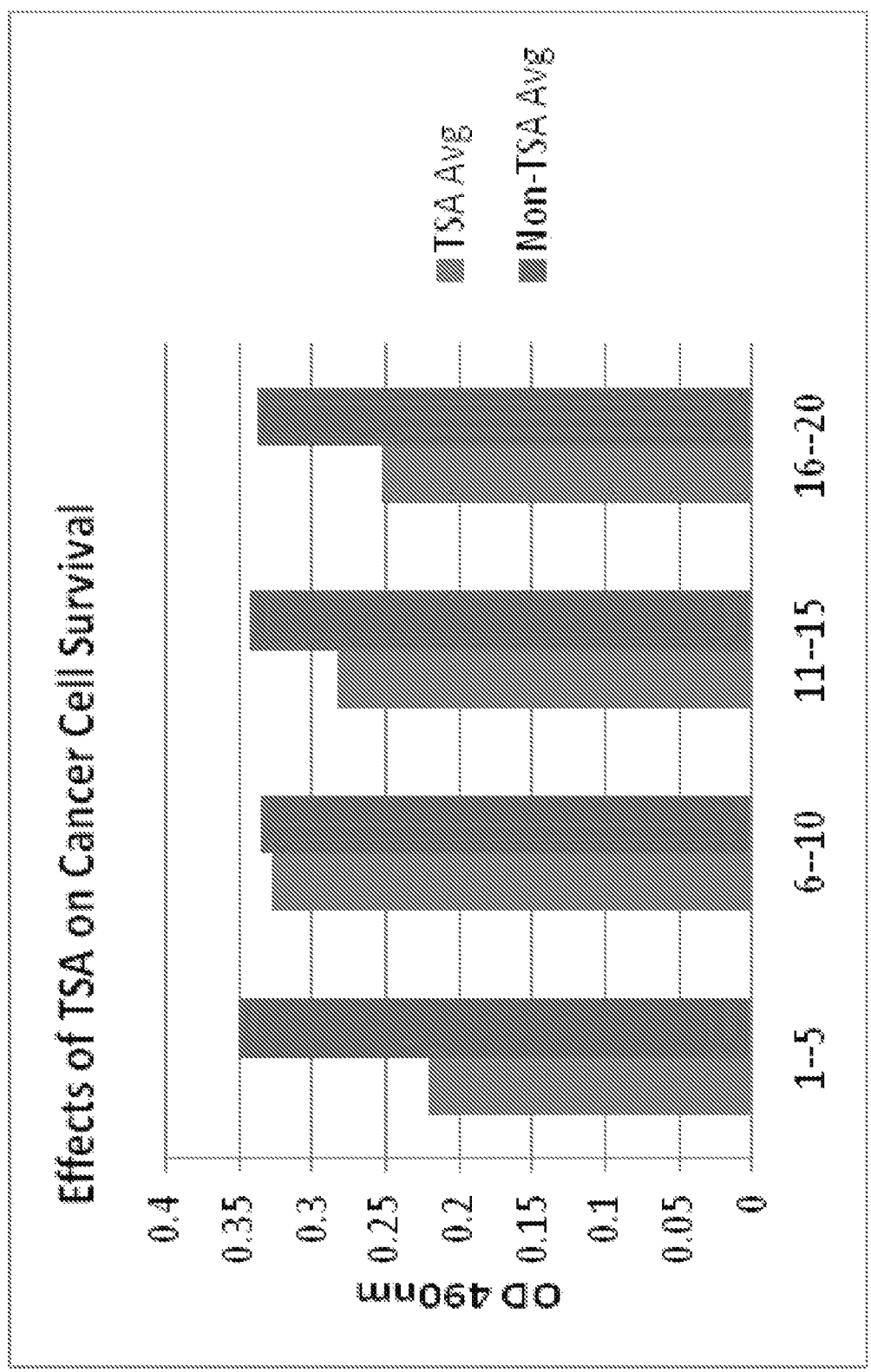
FIG. 1A depicts viability of tumor cells grown in placental cotyledons in the presence (leftmost, light colored bars) and absence (rightmost, dark colored bars) of Trichostatin A (TSA). Cells from twenty samples of the cotyledon were counted, and cell viability for four groups from the total of twenty samples are presented as samples 1-5, 6-10, 11-15, and 16-20.

Provided herein are methods of evaluating potential antitumor compounds, and of identifying antitumor compounds, comprising contacting tumor cells comprised on or in a placenta, or portion thereof, with the potential antitumor compound, and evaluating the effect of the potential antitumor compound on the tumor cells, wherein if the potential antitumor compound has a greater effect on the tumor cells than is seen in appropriate controls, e.g., as described below, the potential antitumor compound is identified as an antitumor compound. Without wishing to be bound by theory, the placenta provides a three-dimensional growth environment for tumor cells that more closely resembles the natural in vivo growth environment of the cells, thus providing a more accurate system for evaluating the efficacy of potential antitumor compounds. Generally, in the context of the present method, if the potential antitumor compound slows the growth of the tumor cells, reduces the viability of the tumor cells, reduces the number or mass of the tumor cells, reduces the number of the tumor cells to below the rate of tumor cell proliferation, or kills the tumor cells, the potential antitumor compound is identified as an antitumor compound.

A "potential antitumor compound," as used herein, encompasses novel compounds, known compounds that have not been tested against a particular tumor cell type or tumor cell line, or compounds known to have at least some effect against a particular tumor cell type or tumor cell line, but have not been tested against another tumor cell type, or according to the present methods. As used herein, "tumor" includes tumor cells, tumor stem cells, cancer stem cells, or any type of tumor cell line, and includes solid tumors, hematological cancers, and the like.

Reference herein to a "placenta" includes a whole placenta or a portion thereof, and includes a decellularized placenta (e.g., a placental matrix) unless otherwise stated. A "portion" of a placenta indicates a structural portion of a placenta, e.g., a section or wedge of a placenta, a placental lobule or cotyledon, the amnion, the chorion, or the umbilical cord, or the like, whether cellularized or decellularized. Portions of a placenta useful in the methods provided herein can be small enough, e.g., to fit within a 12-, 48-, or 96-well plate. The term does not, however, encompass solely isolated placental collagen.

4.1. Methods of Assessing Potential Antitumor Compounds, and Identifying Antitumor Compounds As provided herein, the method evaluates the effectiveness of a potential antitumor compound against tumor cells using a construct comprising a placenta that comprises the tumor cells. The tumor cells are contacted with the potential antitumor compound in the context of the construct. The tumor cells can be comprised on, or within, or both, the placenta. The placenta may be a whole, cellularized placenta, e.g., a placenta as obtained from a normal vaginal birth or from a Caesarian section. The method may use a portion of a placenta, e.g., a cross-section of a placenta, a part of a placenta dissected from other parts, a particular anatomical structure of a placenta, or the like. In certain embodiments, the placenta, or portion thereof, is decellularized in part or in whole. In preferred embodiments of either a cellularized or decellularized placenta, or portion thereof, the placenta, or portion thereof, has a substantially intact vasculature; that is, a vasculature through which a fluid can be passaged into, and back out of, the placenta or portion thereof with the loss of, e.g., less than 5%, 10%, 15%, 20%, or 25% of input volume. Methods of decellularizing placenta tissue, including methods that leave the vasculature substantially intact, are presented below.

In one embodiment, the method comprises the contacting of the potential antitumor compound with tumor cells on or in the placenta or portion thereof. In certain embodiments, the tumor cells can be seeded onto or into the placenta, e.g., in liquid suspension in any physiologically-acceptable fluid, e.g., a saline solution, culture medium, or the like. In a preferred embodiment, the placenta or portion thereof has a substantially intact vasculature, and the tumor cells are introduced into the placenta or portion thereof by passaging the physiologically-acceptable liquid comprising the tumor cells through the vasculature such that at least a portion of the tumor cells are retained within the vasculature. In embodiments in which a whole placenta or substantial portion thereof is used, the placenta may be contained, e.g., within a flat, open container, e.g., a tray or pan, or may be contained within a closed container, e.g., a bag.

A portion of the placenta may be used in the methods presented herein. In certain embodiments, the portion is shaped to allow containment by a container. The container may, for example, be any physiologically-acceptable container used, e.g., for cell or tissue culture, e.g., plastic or glass culture dishes, flasks, or multiwall plates. In certain embodiments, the container allows for the periodic, or continuous, flow of fluid in and or around the placenta or portion thereof. In other embodiments, the placenta or portion thereof is contained within a bioreactor, e.g., a commercially-available bioreactor.

In any of the embodiments herein, the placenta or portion thereof is preferably contained within a container that allows for the administration of tumor cells to the placenta, and of a potential antitumor compound to the tumor cells, as well as allowing for one or more forms of analysis of the number or mass of tumor cells, e.g., before, during, and/or after contacting the tumor cells with the potential antitumor compound.

Tumor cells may be introduced into the placenta or portion thereof and cultured prior to contacting with said potential antitumor compound, e.g., for 1, 2, 3, 4, 5, 6, 7, 8, 9, 10, 11, 12, 13, 14, 15, 16, 17, 18, 19, 20, 21, 22, 23 or 24 hours, or for 2, 3, 4, 5, 6, 7, 8, 9, 10, 11, 12, 13 or 14 days, or more. In certain other embodiments, the tumor cells are introduced into the placenta or portion thereof at the same time as the potential antitumor compound.

In a specific embodiment, non-tumor cells can additionally be introduced into the placenta or portion thereof. For example, the non-tumor cells can be, e.g., stromal cells, e.g., adipose stromal cells, bone marrow-derived stromal cells, or the like. Advantageously, the stromal cells may be introduced into the placenta or portion thereof prior to introduction of the tumor cells, e.g., for a time sufficient to allow establishment of the stromal cells. The ratio of numbers of tumor cells to numbers of stromal cells can be, e.g., about 1:1, 1:2, 1:3, 1:4, 1:5, 1:6, 1:7, 1:8, 1:9, 1:10, 1:12, 1:14, 1:16, 1:18, 1:20, 1:25, 1:30, or more. The stromal cells may be cultured, e.g., for about 1, 2, 3, 4, 5, 6, 7, 8, 9, 10, 11, 12, 13, 14, 15, 16, 17, 18, 19, 20, 21, 22, 23 or 24 hours, or for 2, 3, 4, 5, 6, 7, 8, 9, 10, 11, 12, 13 or 14 days, or more, prior to introduction of the tumor cells into the placenta or portion thereof. The stromal cells and tumor cells may be introduced into the placenta or portion thereof at the same time, e.g., in separate solution administrations, or as a co-suspension of cells.

In certain other embodiments, the non-tumor cells may be, e.g., stem cells, for example, mesenchymal stem cells or placental stem cells. Mesenchymal stem cells suitable for use in the methods provided herein are described, e.g., in U.S. Pat. No. 5,486,359, the disclosure of which is hereby incorporated by reference in its entirety. Placental stem cells suitable for use in the methods provided herein are described, e.g., in U.S. Pat. Nos. 7,468,276 and 8,057,788, the disclosures of which are hereby incorporated by reference herein in their entireties.

The method, in certain embodiments, can be used to identify new antitumor compounds, that is, antitumor compounds not previously identified as antitumor compounds in any context. In other embodiments, the method can be used to identify new tumors against which compound, already identified as an antitumor compound with respect to one tumor type, is an antitumor compound. In other embodiments, the method can be used to identify, or confirm, compounds that have an antitumor effect on tumor cells from a particular individual.

4.2. Visualizing Tumor Cells and the Effect of Potential Antitumor Compounds The method of evaluating potential antitumor compounds, or of identifying antitumor compounds, disclosed herein is based on identification of compounds that reduce the rate of proliferation of tumor cells in the placenta, or kill tumor cells, or both. The method, in certain embodiments, comprises determining at least a first number of tumor cells prior to contacting the tumor cells with the potential antitumor compound, and at least a second number of tumor cells after contacting the tumor cells with the potential antitumor compound, wherein if said second number is less than said first number, said potential antitumor compound is identified as an antitumor compound. Typically, a control is performed in parallel comprising a placenta comprising tumor cells, equivalent to the experimental condition, except that the tumor cells are not contacted with the potential antitumor compound. For example, a third (control) number of tumor cells can be obtained from such a tumor cell population at the same time as the first number of tumor cells is obtained, and a fourth, control, number of tumor cells can be obtained at the same time as said second number of tumor cells is obtained. In this case, if the difference between the second number of tumor cells and the first number of tumor cells is greater than the difference between the fourth number of tumor cells and the third number of tumor cells, the potential antitumor compound is identified as an antitumor compound. The numbers of tumor cells before and after contacting can, of course, be obtained multiple times, and can be obtained from multiple experimental conditions, and optionally control conditions, in parallel.

As such, in preferred embodiments, the tumor cells are tagged or labeled in some way so as to make them quantifiable during performance of the method. The amount of tagging or labeling is preferably strongly correlated with the number of tumor cells. In certain embodiments, the tumor cells are labeled with, e.g., fluorescent labels or radioactive labels. In a specific embodiment, the label is attached to an antibody. Such an antibody can, e.g., recognize a tumor-specific antigen on said tumor cells, or can recognize an antigen specific to said tumor cells. Determining the amount of a label present in the assay, in certain embodiments, is used as a proxy for determining the number, or amount, of tumor cells present at any point during the performance of the method, e.g., either or both of before or after contacting with the potential antitumor compound.

Fluorescence values, e.g., the aggregate fluorescence of a portion or the whole of tumor cells used in the method, can be used as a surrogate for numbers of tumor cells, and can be used to determine if a potential antitumor compound reduces the number of tumor cells, or reduces the growth rate of the tumor cells. In certain embodiments, the method comprises obtaining at least a first fluorescence value from the placenta prior to contacting the tumor cells with the potential antitumor compound, and obtaining at least a second fluorescence value from the placenta after contacting the tumor cells with the potential antitumor compound, and comparing the first and second fluorescence values. Typically, a control is performed in parallel comprising a placenta comprising tumor cells, equivalent to the experimental condition, except that the tumor cells are not contacted with the potential antitumor compound; for example, a third, control, fluorescence value can be obtained from such a tumor cell population at the same time as the first fluorescence value is obtained, and a fourth, control, fluorescence value can be obtained at the same time as said second fluorescence value is obtained. Other control fluorescence values may be obtained, of course. If the second fluorescence value is less than the first fluorescence value, the potential antitumor compound is identified as an antitumor compound. More specifically, if the difference between the second fluorescence level and the first fluorescence value is greater than the difference between the fourth fluorescence value and the third fluorescence value, the potential antitumor compound is identified as an antitumor compound.

In certain embodiments, the potential antitumor compound reduces the rate of proliferation or growth of the tumor cells. In this case, the rate of increase of fluorescence after the tumor cells are contacted with the potential antitumor compound would be less than the rate of increase of fluorescence for control cells. In a specific embodiment, e.g., where the potential antitumor compound kills tumor cells faster than the tumor cells can proliferate, the difference between said second number of tumor cells and said first number of tumor cells is determined by labeling said tumor cells with a fluorescent antibody; assigning a first fluorescence value to said first number of tumor cells, and a second fluorescence value to said second number of tumor cells; and determining the difference between said second fluorescence value and said first fluorescence value, wherein said difference is correlated to said difference between said second number of tumor cells and said first number of tumor cells. In another embodiment, e.g., said tumor cells are labeled with a fluorescent antibody, and wherein if there is a decrease in fluorescence from said fluorescent antibody after said contacting compared to before said contacting, said potential antitumor compound is an antitumor compound. In another specific embodiment, e.g., wherein the potential antitumor compound slows growth of the tumor cells, the difference between said second number of tumor cells and said first number of tumor cells, and between said third number of tumor cells and said first number of tumor cells, is determined by labeling said tumor cells with a fluorescent antibody; assigning a first fluorescence value to said first number of tumor cells, a second fluorescence value to said second number of tumor cells, and a third fluorescence value to said third number of tumor cells; and determining the difference between said second fluorescence value and said first fluorescence value, wherein said difference is correlated to said difference between said second number of tumor cells and said first number of said tumor cells, and determining the difference between said third fluorescence value and said first fluorescence value, wherein said difference is correlated to said difference between said third number of tumor cells and said first number of tumor cells. In certain embodiments, the tumor cells are labeled with a fluorescent antibody, and wherein if there is a decrease in the rate of increase in fluorescence from said fluorescent antibody over time after said contacting, as compared to a rate of increase in fluorescence from said fluorescent antibody before said contacting, said potential antitumor compound is an antitumor compound.

In other embodiments, tumor cells can be visualized, and therefore quantitated, using, e.g., a colorimetric assay, e.g., a colorimetric assay measuring mitochondrial activity. Dyes useful for such an assay include, but are not limited to, MTT (3-(4,5-Dimethylthiazol-2-yl)-2,5-diphenyltetrazolium bromide), MTS (3-(4,5-dimethylthiazol-2-yl)-5-(3-carboxymethoxyphenyl)-2-(4-sulfophenyl)-2H-tetrazolium), XTT (2,3-bis-(2-methoxy-4-nitro-5-sulfophenyl)-2H-tetrazolium-5-carboxanilide), WST-1 (4-[3-(4-iodophenyl)-2-(4-nitrophenyl)-2H-5-tetrazolio]-1,3-benzene disulfonate), WST-8 (2-(2-methoxy-4-nitrophenyl)-3-(4-nitrophenyl)-5-(2,4-disulfophenyl)-2H-tetrazolium, or the like. Standard assays using the dyes are well-known in the art. In the context of the methods provided herein, the number of tumor cells, or size of tumor mass(es) in the placenta can be extrapolated from the amount of quantifiable color obtained using the dyes. Typically, the amount of color resulting from such dyes is positively correlated with the number, or amount, of tumor cells in the placenta. Typically, such a colorimetric assay is performed by passaging of the dye, and in certain embodiments, accessory molecules, through the placenta in which the tumor cells are resident as part of the method of identifying antitumor compounds, or assessing potential antitumor compounds, e.g., in a volume of cell culture medium. A sample of the medium that has been passaged through the placenta is obtained, and assayed using the dye.

The method can comprise obtaining at least one colorimetric reading prior to contacting the tumor cells with the potential antitumor compound, and at least one colorimetric reading after said contacting, where a colorimetric reading is an absorbance value at a designated wavelength for the particular dye being used. Typically, a control omitting the potential antitumor compound will be performed in parallel with the experimental condition testing the potential antitumor compound, in which case a third absorbance value is obtained prior to contacting said tumor cells with said potential antitumor compound, and a fourth absorbance value after contacting the tumor cells with the potential antitumor compound. In embodiments in which the potential antitumor compound kills tumor cells, at least a first absorbance value is obtained prior to contacting the tumor cells with the potential antitumor compound, and at least a second absorbance value is obtained after contacting the tumor cells with the potential antitumor compound, wherein is the second absorbance value is less than the first absorbance value, the potential antitumor compound is an antitumor compound. In embodiments in which the potential antitumor compound kills the cells, or reduces the growth or proliferation rate of the tumor cells, if the difference between said second and said first absorbance values is greater than the difference between said fourth absorbance value and said third absorbance value, the potential antitumor compound is identified as an antitumor compound.

In other embodiments, tumor cells can be visualized, and therefore quantitated, using, e.g., a DNA synthesis assay. In such an assay, for example, BrdU can be introduced to the tumor cells in the placenta or portion thereof, and visualized using, e.g., fluorescent antibodies as described above. The amount of BrdU is positively correlated with the amount of tumor cell proliferation; as such, a reduction in the amount of incorporated BrdU, or a reduction in the rate of increase of BrdU by the tumor cells, as compared to an appropriate control, as a result of contacting the tumor cells with a potential anticancer compound, indicates that the potential anticancer compound is an anticancer compound.

In other embodiments, the number or amount of tumor cells in the method can be determined, e.g., using a permeability assay, and determining the number of cells that either take up a dye, or the number of cells that exclude a dye, e.g., trypan blue, lactate dehydrogenase, ethidium homodimer-1, or the like.

In other embodiments, the number or amount of tumor cells in the method can be determined, e.g., using an apoptosis assay. Apoptosis assays, which can use, e.g., samples of culture medium passaged through the tumor cell-containing placenta, are well-known in the art. Many kits have been developed for the assay in this category and can be performed in multiwell plates with great sensitivity. Apoptosis assays useful in the present methods include, e.g., bioluminescent caspase assays including for the detection of caspase-3/7, caspase-8, caspase-9, caspase-2 and caspase-6 activities; terminal deoxyribonucleotidyl transferase dUTP nick end labeling (TUNEL) assays; Annexin V/PI assays; mitochondrial apoptosis assay (JC-1), and the like.

The method can comprise obtaining at least one amount of apoptosis in the tumor cell population in the placenta ("apoptosis value") prior to contacting the tumor cells with the potential antitumor compound, and at least one apoptosis value after said contacting. Typically, a control omitting the potential antitumor compound will be performed in parallel with the experimental condition testing the potential antitumor compound, in which case a third apoptosis value is obtained prior to contacting said tumor cells with said potential antitumor compound, and a fourth apoptosis value after contacting the tumor cells with the potential antitumor compound. In embodiments in which the potential antitumor compound kills tumor cells, at least a first apoptosis value is obtained prior to contacting the tumor cells with the potential antitumor compound, and at least a second apoptosis value is obtained after contacting the tumor cells with the potential antitumor compound, wherein if the second apoptosis value is less than the first apoptosis value, the potential antitumor compound is an antitumor compound. In embodiments in which the potential antitumor compound kills the cells, or reduces the growth or proliferation rate of the tumor cells, if the difference between said second and said first apoptosis values is greater than the difference between said fourth apoptosis value and said third apoptosis value, the potential antitumor compound is identified as an antitumor compound.

In specific embodiments of any of the above embodiments, another cell type, e.g., vascular endothelial cells, fibroblasts, or the like, can be used as a separate control to determine if the effect of the antitumor compound is specific to the tumor cells or not. In such embodiments, a fifth parameter (fluorescence value, absorbance value, apoptosis value, or the like) is obtained before contacting said tumor cell with said potential antitumor compound, and a sixth parameter is obtained after contacting said tumor cell with said potential antitumor compound, wherein said potential antitumor compound is identified as an antitumor compound if (a)(i) said second parameter is larger than said first parameter, and (ii) the difference between said second parameter and said first parameter is greater than the difference between said sixth parameter and said fifth parameter; or (b) (i) the difference between said fourth parameter and said third parameter is less than the difference between the second parameter and the first parameter, and (ii) the difference between said second parameter and said first parameter is greater than the difference between said sixth parameter and said fifth parameter.

4.3. Methods of Obtaining Placenta

Generally, a human placenta is recovered shortly after its expulsion after normal birth, or after a Caesarian section. In a preferred embodiment, the placenta is recovered from a patient after informed consent and after a complete medical history of the patient is taken and is associated with the placenta. Preferably, the medical history continues after delivery. Such a medical history can be used to coordinate subsequent use of the placenta or the stem cells harvested therefrom. For example, human placental stem cells can be used, in light of the medical history, for personalized medicine for the infant associated with the placenta, or for parents, siblings or other relatives of the infant.

The umbilical cord blood and placental blood are removed, and can be used for other purposes or discarded. In certain embodiments, after delivery, the cord blood in the placenta is recovered. The placenta can be subjected to a conventional cord blood recovery process. Typically a needle or cannula is used, with the aid of gravity, to exsanguinate the placenta (see, e.g., Anderson, U.S. Pat. No. 5,372,581; Hessel et al., U.S. Pat. No. 5,415,665). The needle or cannula is usually placed in the umbilical vein and the placenta can be gently massaged to aid in draining cord blood from the placenta. Such cord blood recovery may be performed commercially, e.g., by LifeBank USA, Cedar Knolls, N.J. Preferably, the placenta is gravity drained without further manipulation so as to minimize tissue disruption during cord blood recovery.

Typically, a placenta is transported from the delivery or birthing room to another location, e.g., a laboratory, for recovery of cord blood and collection of stem cells by, e.g., perfusion or tissue dissociation. The placenta is preferably transported in a sterile, thermally insulated transport device (maintaining the temperature of the placenta between about 20° C. to about 28° C.), for example, by placing the placenta, with clamped proximal umbilical cord, in a sterile zip-lock plastic bag, which is then placed in an insulated container. In another embodiment, the placenta is transported in a cord blood collection kit substantially as described in pending U.S. Pat. No. 7,147,626. Preferably, the placenta is delivered to the laboratory four to twenty-four hours following delivery. In certain embodiments, the proximal umbilical cord is clamped, preferably within 4-5 cm (centimeter) of the insertion into the placental disc prior to cord blood recovery. In other embodiments, the proximal umbilical cord is clamped after cord blood recovery but prior to further processing of the placenta.

The placenta can be stored under sterile conditions and at either room temperature or at a temperature of 5° C. to 25° C. The placenta may be stored for a period of for a period of four to twenty-four hours, up to forty-eight hours, or longer than forty eight hours, prior to perfusing the placenta to remove any residual cord blood. In one embodiment, the placenta is harvested from between about zero hours to about two hours post-expulsion. The placenta is preferably stored in an anticoagulant solution at a temperature of 5° C. to 25° C. Suitable anticoagulant solutions are well known in the art, e.g., a solution of heparin or warfarin sodium. In a preferred embodiment, the anticoagulant solution comprises a solution of heparin (e.g., 1% w/w in 1:1000 solution). The exsanguinated placenta is preferably stored for no more than 36 hours before placental stem cells are collected.

Typically the placenta is perfused prior to use in the present methods, e.g., prior to decellularization. The perfusion may, for example, be for no other purpose than to remove blood from the placenta. However, the placenta may be perfused, e.g., to collect placental stem cells and/or placental perfusate cells, e.g., as described in U.S. Pat. No. 7,468,276, the disclosure of which is hereby incorporated by reference in its entirety.

4.4. Methods of Decellularizing Placenta

Once the placenta is prepared as above, and optionally perfused, it is optionally decellularized, e.g., in such a manner as to preserve the native structure of the placental vasculature, e.g., so as to leave the placental vasculature substantially intact. As used herein, "substantially intact" means that the placental vasculature (e.g., decellularized placental scaffold) remaining after decellularization retains all, or most, of the gross structure of the placental vasculature prior to decellularization such that a fluid can be passed into, and back out of, the placenta or portion thereof with the loss of, e.g., less than 5%, 10%, 15%, 20%, or 25% of input volume. In certain embodiments, the placental vasculature is capable of being re-seeded, e.g., with vascular endothelial cells or other cells, so as to recreate the placental vasculature.

Placental tissue may be sterilized, e.g., by incubation in a sterile buffered nutrient solution containing antimicrobial agents, for example an antibacterial, an antifungal, and/or a sterilant compatible with the transplant tissue. The sterilized placental tissue may then be cryopreserved for further processing at a later time or may immediately be further processed according to the next steps of this process including a later cryopreservation of the tissue matrix or other tissue products of the process.

Several methods of reducing the viability of native cells in tissues and organs are known, including physical, chemical, and biochemical methods. See, e.g. U.S. Pat. No. 5,192,312 (Orton) which is incorporated herein by reference. Such methods may be employed in accordance with the process described herein. However, the decellularization technique employed preferably does not result in gross disruption of the anatomy of the placental tissue or substantially alter the biomechanical properties of its structural elements, and preferably leaves the placental vasculature substantially intact. In certain embodiments, the treatment of the placental tissue to produce a decellularized tissue matrix does not leave a cytotoxic environment that mitigates against subsequent repopulation of the matrix with cells that are allogeneic or autologous to the recipient. As used herein, cells and tissues that are "allogeneic" to the recipient are those that originate with or are derived from a donor of the same species as a recipient of the placental matrix, and "autologous" cells or tissues are those that originate with or are derived from a recipient of the placental matrix.

Physical forces, for example the formation of intracellular ice, can be used to decellularize transplant tissues. As such, in certain embodiment, the placenta is first cryopreserved as part of decellularization. For example, vapor phase freezing (slow rate of temperature decline) of placental tissue can be performed. Optionally, the placental tissue is cryopreserved in the presence of one or more cryoprotectants. Colloid-forming materials may be added during freeze-thaw cycles to alter ice formation patterns in the tissue. For example, polyvinylpyrrolidone (10% w/v) and dialyzed hydroxyethyl starch (10% w/v) may be added to standard cryopreservation solutions (DMEM, 10% DMSO, 10% fetal bovine serum) to reduce extracellular ice formation while permitting formation of intracellular ice.

In certain embodiments, various enzymatic or other chemical treatments to eliminate viable native cells from implant tissues or organs may be used. For instance, extended exposure of cells to proteases such as trypsin result in cell death.

In certain other embodiments, the placental tissue is decellularized using detergents or combinations thereof, for example, a nonionic detergent, e.g., Triton X-100, and an anionic detergent, e.g., sodium dodecyl sulfate, may disrupt cell membranes and aid in the removal of cellular debris from tissue. Preferably, residual detergent in the decellularized tissue matrix is removed, e.g., by washing with a buffer solution, so as to avoid interference with the later repopulating of the tissue matrix with viable cells.

The decellularization of placental tissue is preferably accomplished by the administration of a solution effective to lyse native placental cells. Preferably, the solution is an aqueous hypotonic or low ionic strength solution formulated to effectively lyse the cells. In certain embodiments, the aqueous hypotonic solution is, e.g. deionized water or an aqueous hypotonic buffer. In specific embodiments, the aqueous hypotonic buffer contains one or more additives that provide sub-optimal conditions for the activity of one or more proteases, for example collagenase, which may be released as a result of cellular lysis. Additives such as metal ion chelators, for example 1,10-phenanthroline and ethylenediaminetetraacetic acid (EDTA), create an environment unfavorable to many proteolytic enzymes. In other embodiments, the hypotonic lysis solution is formulated to eliminate or limit the amount of divalent cations, e.g., calcium and/or zinc ions, available in solution, which would, in turn, reduce the activity of proteases dependent on such ions.

Preferably, the hypotonic lysis solution is prepared selecting conditions of pH, reduced availability of calcium and zinc ions, presence of metal ion chelators and the use of proteolytic inhibitors specific for collagenase such that the solution will optimally lyse the native cells while protecting the underlying tissue matrix from proteolytic degradation. In certain embodiments, a hypotonic lysis solution may include a buffered solution of water, pH 5.5 to 8, preferably pH 7 to 8, free or substantially free from calcium and zinc ions, and/or including a metal ion chelator such as EDTA. Additionally, control of the temperature and time parameters during the treatment of the tissue matrix with the hypotonic lysis solution may also be employed to limit the activity of proteases.

In some embodiments, decellularization of placental tissue includes treatment of the tissue with one or more nucleases, e.g., effective to inhibit cellular metabolism, protein production and cell division without degrading the underlying collagen matrix. Nucleases that can be used for digestion of native cell DNA and RNA include either or both of exonucleases or endonucleases. Suitable nucleases for decellularization are commercially available. For example, exonucleases that effectively inhibit cellular activity include DNAase I (SIGMA Chemical Company, St. Louis, Mo.) and RNAase A (SIGMA Chemical Company, St. Louis, Mo.) and endonucleases that effectively inhibit cellular activity include EcoRI (SIGMA Chemical Company, St. Louis, Mo.) and Hind III (SIGMA Chemical Company, St. Louis, Mo.).

Selected nucleases may be contained in a physiological buffer solution which contains ions that are optimal for the activity of the nuclease, e.g., magnesium salts or calcium salts. It is also preferred that the ionic concentration of the buffered solution, the treatment temperature and the length of treatment are selected to assure the desired level of effective nuclease activity. The buffer is preferably hypotonic to promote access of the nucleases to cell interiors. In certain embodiments, the one or more nucleases comprise DNAase I and RNAase A. Preferably, the nuclease degradation solution contains about 0.1 microgram/mL to about 50 microgram/mL, or about 10 microgram/mL, of the nuclease DNAase I, and about 0.1 microgram/mL to about 10 microgram/mL, preferably about 1.0 microgram/mL, of RNAase A. The placental tissue may be decellularized by application of the foregoing enzymes at a temperature of about 20° C. to 38° C., preferably at about 37° C., e.g., for about 30 minutes to 6 hours.

In other embodiments, the decellularization solution comprises one or more phospholipases, e.g. phospholipase A and/or phospholipase C, e.g., in a buffered solution. Preferably, the phospholipase as used should not have a detrimental effect on the tissue matrix protein. The pH of the vehicle, as well as the composition of the vehicle, will also be adjusted with respect to the pH activity profile of the enzyme chosen for use. Moreover, the temperature applied during application of the enzyme to the tissue is, in various embodiments, adjusted in order to optimize enzymatic activity.

Following decellularization, the tissue matrix in certain embodiments is washed in a wash solution to assure removal of cell debris which may include cellular protein, cellular lipids, and cellular nucleic acid, as well as any extracellular debris. Removal of this cellular and extracellular debris reduces the likelihood of the transplant tissue matrix eliciting an adverse immune response from the recipient upon implant. For example, the tissue may be washed one or more times with a wash solution, wherein the wash solution is, e.g., PBS or Hanks' Balanced Salt Solution (HBSS). The composition of the balanced salt solution wash, and the conditions under which it is applied to the transplant tissue matrix may be selected to diminish or eliminate the activity of proteases or nucleases utilized during the decellularization process. In specific embodiments, the wash solution does not contain magnesium or calcium, e.g. magnesium salts or calcium salts, and the washing process proceeds at a temperature of between about 2° C. and 42° C., e.g., 4° C. most preferable. The transplant tissue matrix may be washed, e.g., incubated in the balanced salt wash solution for up to 1, 2, 3, 4, 5, 6, 7, 8, 9, 10, 11 or 12 days, e.g., with changes in wash solution every –13 days. Optionally, an antibacterial, an antifungal or a sterilant or a combination thereof, may be included in the wash solution to protect the transplant tissue matrix from contamination with environmental pathogens. Washing may be performed by soaking the placental tissue with or without mild agitation.

The tissue matrix, once decellularized, can be preserved by cryopreservation. Techniques of cryopreservation of tissue are well known in the art. See, e.g., Brockbank, K. G. M., "Basic Principles of Viable Tissue Preservation," In: *Transplantation Techniques and Use of Cryopreserved Allograft Cardiac Valves and Vascular Tissue*, D. R. Clarke (ed.), Adams Publishing Group, Ltd., Boston. pp 9-23 (discussing cryopreservation of tissues and organs).

The tissue matrix, whether or not having been cryopreserved, in certain embodiments is treated to enhance the adhesion and inward migration of the allogeneic or autologous cells, in vitro, which will be used to repopulate the transplant tissue.

In certain embodiments, attachment of autologous or allogeneic cells to decellularized placental matrix may be increased, e.g., by contacting the placental matrix with serum (human or fetal bovine, maximal binding with 1% serum) and/or purified fibronectin, e.g., in culture medium in which the decellularized placental matrix is placed, e.g., in preparation for repopulation with allogeneic or autologous cells. Each of the two homologous subunits of fibronectin has two cell recognition regions, including one comprising the Arg-Gly-Asp (RGD) sequence. A second site, binding glycosaminoglycans, acts synergistically and appears to stabilize the fibronectin-cell interactions mediated by the RGD sequence.

As such, in a specific embodiment, the decellularized placental matrix is contacted with both fibronectin and a glycosaminoglycan, e.g., heparin, for a period effective for binding of the fibronectin to surfaces of the placental matrix to be repopulated with allogeneic or autologous cells. The fibronectin, and optionally glycosaminoglycan, can be included within a physiologically-acceptable buffer or culture medium, e.g., sodium phosphate/glycerin/bovine serum albumin and Dulbecco's Modified Eagle's Medium (DMEM) (e.g., GIBCO). The buffer or culture medium is preferably maintained at a physiologically acceptable pH, e.g., about 6.8 to 7.6. Fibronectin may be obtained from human blood, processed to limit contamination with virus, or may be obtained from commercial sources. The concentration of fibronectin and/or glycoprotein may range from about 1 microgram/mL to about 100 microgram/mL, e.g., about 10 microgram/mL. The preferred weight ratio of fibronectin to heparin is about 100:1 to about 1:100, or about 10:1 to about 1:10, e.g., 10:1 fibronectin:glycosaminoglycan, e.g. heparin.

The decellularized placental matrix may be contacted with, e.g., treated with, one or more compositions that act, e.g., to enhance cell chemotaxis, increasing the rate of directional movement along a concentration gradient of the substance in solution. With respect to fibroblast cells, fibroblast growth factor, platelet-derived growth factor, transforming growth factor-beta (TGF-β), fibrillar collagens, collagen fragments, and fibronectin are chemotactic.

In a specific, preferred embodiment, the placenta is decellularized as follows. Placental tissue from which blood has been removed is first frozen at −20° C. to −180° C., e.g., about −80° C. The tissue is then thawed at about 4° C. overnight. The thawed tissue is then digested with 0.1% trypsin at room temperature for 2 hours to produce digested placental tissue. The digested tissue is then treated sequentially with 1%, 2% and 3% Triton-X100 for 24 hours each. The Triton-X100 treatments are then followed by treatment of the tissue with 0.1% SDS-PBS for 24 h, after which the cellular material is substantially removed. The tissue is then extensively washed with 1-10 changes of phosphate buffered saline (PBS), followed by treatment with DNase I (150 U/mL) for 1 hour at room temperature. Finally, the remaining decellularized placental matrix is again extensively washed with PBS+1% antibiotics (penicillin+streptomycin), optionally dried, and preserved at 4° C.

4.5. Methods of Seeding Cells onto or into the Matrix

Cells may be loaded onto the decellularized placental matrix by any physiologically-acceptable method. In certain embodiments, the cells are suspended in, e.g., a liquid culture medium, salt solution or buffer solution, and the cell-containing liquid is perfused into the placental matrix through one or more of the vascular matrices, e.g., by passage of the cell-containing liquid through the placental vasculature or, in embodiments in which the placenta is decellularized, the substantially intact vascular scaffold. Passage of the cell-containing liquid may be facilitated, e.g., by use of a pump, e.g., a peristaltic pump, to push the liquid into the vasculature of the placenta, optionally with a second pump removing liquid from the placenta. The placental matrix may also be cultured in such a cell-containing liquid culture medium, salt solution or buffer solution for a time sufficient for a plurality of the cells to attach to said placental matrix. In certain other embodiments, the cells, e.g. in liquid suspension, are seeded onto and/or injected directly into, the placenta or decellularized placental scaffolding.

4.6. Cells to be Used

4.6.1. Tumor Cells

Any tumor cell can be used in the context of the present method of evaluating potential antitumor compounds, and of identifying antitumor compounds. The selection of tumor cells for use in the method can depend upon the particular cancer for which an antitumor compound is sought. The method can be used to identify antitumor compounds generally applicable for tumor cells of a particular type of cancer, or can be used to identify antitumor compounds that would be particularly effective in treating a particular individual's cancer.

In certain embodiments, the cells to be used are primary tumor cells. The primary tumor cells can be, e.g., cells from a blood sample or tissue biopsy. The tumor cells can be allogeneic to a particular individual to be treated, or autologous to a particular individual to be treated. In certain other embodiment, said tumor cells are tumor cell line cells. In other embodiments, the tumor cells are tumor stem cells or cancer stem cells. In specific embodiments, said tumor cells are mesothelioma cells, melanoma cells, adenoma cells, carcinoma cells, adenocarcinoma cells, ductal carcinoma cells, leukemia cells, acute myelogenous leukemia cells, acute myeloid leukemia cells, acute T cell leukemia cells, acute lymphoblastic leukemia cells, hairy cell leukemia cells, acute promyelocytic leukemia cells, lymphoma cells, Burkitt's lymphoma cells, non-Hodgkin's lymphoma cells, Hodgkin's lymphoma cells, or multiple myeloma cells. rhabdomyosarcoma cells, osteosarcoma cells, neuroblastoma cells, astrocytoma cells, or glioblastoma cells. In more specific embodiments, said tumor cell line is 5637 (Carcinoma), KHOS/NP (Osteosarcoma), MNNG/HOS (Osteosarcoma), Saos-2 (Osteosarcoma), U-2 OS (Osteosarcoma), SJSA-1 (Osteosarcoma), CCF-STTG1 (Astrocytoma), DBTRG-05MG (Glioblastoma), U87 MG (Glioblastoma), T98G (Glioblastoma), SK-N-SH (Neuroblastoma), SK-N-AS (Neuroblastoma), MCF-7 (Adenocarcinoma), MDA-MB-231 (Adenocarcinoma), MDA-MB-436 (Adenocarcinoma), SK-BR-3 (Adenocarcinoma), BT-20 (Carcinoma), BT-474 (Carcinoma), CAMA-1 (Carcinoma), HCC2218 (Carcinoma), SW527 (Carcinoma), MDA-MB-453 (Carcinoma), MDA-MB-435S (Carcinoma), T-47D (Carcinoma), ZR-75-1 (Carcinoma), UACC-812 (Carcinoma), HCC1419 (Carcinoma), HeLa (Adenocarcinoma), Caco-2 (Adenocarcinoma), COLO205 (Adenocarcinoma), COLO320/DM (Adenocarcinoma), DLD-1 (Adenocarcinoma), HCT-15 (Adenocarcinoma), SK-CO-1 (Adenocarcinoma), SW48 (Adenocarcinoma), SW480 (Adenocarcinoma), HCT-8 (Adenocarcinoma), RKO (Carcinoma), LS411N (Carcinoma), T84 (Carcinoma), AGS (Adenocarcinoma), KATO III (Carcinoma), NCI-N87 (Carcinoma), SNU-16 (Carcinoma), 769-P (Adenocarcinoma), 786-0 (Adenocarcinoma), ACHN (Adenocarcinoma), A-498 (Carcinoma), Caki-1 (Carcinoma), G-402 (Leiomyoblastoma), CML-T1 (Leukemia), CTV-1 (Leukemia), JVM-2 (Leukemia), K562 (Leukemia), MHH-CALL2 (Leukemia), NALM-6 (Leukemia), 8E5 (Leukemia), CCRF-SB (Leukemia), CEM/C1 (Leukemia), CEM/C2 (Leukemia), CEM-CM3 (Leukemia), CCRF-HSB-2 (Leukemia), KG-1 (Leukemia), KG-1a (Leukemia), CCRF-CEM (Leukemia), MOLT-3 (Leukemia), SUP-B15 (Leukemia), TALL-104 (Leukemia), Loucy (Leukemia), RS411 (Leukemia), REH (Leukemia), AML-193 (Leukemia), THP-1 (Leukemia), MOLM-13 (Leukemia), Kasumi-1

(Leukemia), Kasumi-3 (Leukemia), BDCM (Leukemia), HL-60 (Leukemia), 12.1 (Leukemia), 19.2 (Leukemia), J.gamma1.WT (Leukemia), J.RT3-T3.5 (Leukemia), P116 (Leukemia), P116.c139 [P116.c39] (Leukemia), D1.1 (Leukemia), J45.01 (Leukemia), MV-4-11 (Leukemia), Kasumi-4 (Leukemia), MEG-01 (Leukemia), KU812 (Leukemia), Mo (Leukemia), JM1 (Leukemia), GDM-1 (Leukemia), CESS (Leukemia), ARH-77 (Leukemia), SK-HEP-1 (Adenocarcinoma), Bel-7402 (Carcinoma), Bel-7404 (Carcinoma), HEP-3B (Carcinoma), HepG2 (Carcinoma), Calu-3 (Adenocarcinoma), NCI-H1395 (Adenocarcinoma), NCI-H1975 (Adenocarcinoma), SK-LU-1 (Adenocarcinoma), NCI-H2122 (Adenocarcinoma), NCI-H727 (Carcinoid), A-427 (Carcinoma), A549 (Carcinoma), SW1573 (Carcinoma), NCI-H358 (Carcinoma), NCI-H460 (Carcinoma), NCI-H292 (Carcinoma), NCI-H82 (Carcinoma), NCI-H226 (Carcinoma), NCI-H526 (Carcinoma), or MSTO-211H (Mesothelioma)

4.6.2. Non-Tumor Cells

In certain embodiments, the method comprises introducing one or more non-tumor cell types into the placenta, e.g., prior to contacting the tumor cells with the potential antitumor compound. The non-tumor cells can be introduced into the placenta before introduction of the tumor cells, e.g., for a time sufficient for at least a portion of, or substantially all of the non-tumor cells to attach to the placenta; or can be introduced at the same time as introduction of the tumor cells, e.g., as a co-suspension of tumor cells and non-tumor cells, or as separate batches of tumor cells and non-tumor cells. The ratio of numbers of tumor cells to numbers of non-tumor cells can be, e.g., about 1:1, 1:2, 1:3, 1:4, 1:5, 1:6, 1:7, 1:8, 1:9, 1:10, 1:12, 1:14, 1:16, 1:18, 1:20, 1:25, 1:30, or more. The stromal cells may be cultured, e.g., for about 1, 2, 3, 4, 5, 6, 7, 8, 9, 10, 11, 12, 13, 14, 15, 16, 17, 18, 19, 20, 21, 22, 23 or 24 hours, or for 2, 3, 4, 5, 6, 7, 8, 9, 10, 11, 12, 13 or 14 days, or more, prior to introduction of the tumor cells into the placenta or portion thereof.

For example, the non-tumor cells can be, e.g., stromal cells, e.g., adipose stromal cells, bone marrow-derived stromal cells, unprocessed bone marrow, or the like. Advantageously, the stromal cells may be introduced into the placenta or portion thereof prior to introduction of the tumor cells, e.g., for a time sufficient to allow establishment of the stromal cells. The ratio of numbers of tumor cells to numbers of stromal cells can be, e.g., about 1:1, 1:2, 1:3, 1:4, 1:5, 1:6, 1:7, 1:8, 1:9, 1:10, 1:12, 1:14, 1:16, 1:18, 1:20, 1:25, 1:30, or more. The stromal cells may be cultured, e.g., for about 1, 2, 3, 4, 5, 6, 7, 8, 9, 10, 11, 12, 13, 14, 15, 16, 17, 18, 19, 20, 21, 22, 23 or 24 hours, or for 2, 3, 4, 5, 6, 7, 8, 9, 10, 11, 12, 13 or 14 days, or more, prior to introduction of the tumor cells into the placenta or portion thereof. The stromal cells and tumor cells may be introduced into the placenta or portion thereof at the same time, e.g., in separate solution administrations, or as a co-suspension of cells.

In certain other embodiments, the non-tumor cells comprise one or more types of cells of the immune system, e.g., hematopoietic stem cells, hematopoietic precursor cells, T cells, B cells, dendritic cells, macrophages, eosinophils, basophils, neutrophils, and/or natural killer (NK) cells. In a specific embodiment, said NK cells comprise, or are, $CD56^+$ $CD16^-$ placental intermediate natural killer (PiNK) cells, e.g., the placental NK cells described in US 2009/0252710, the disclosure of which is hereby incorporated by reference in its entirety.

In certain other embodiments, the non-tumor cells comprise isolated stem cells or progenitor cells. In specific embodiments, said isolated stem cells or progenitor cells are isolated embryonic stem cells, embryonic germ cells, induced pluripotent stem cells, mesenchymal stem cells, bone marrow-derived mesenchymal stem cells, bone marrow-derived mesenchymal stromal cells, tissue plastic-adherent placental stem cells (PDAC™, e.g., the placental stem cells described in U.S. Pat. Nos. 7,468,276 and 8,057,788, the disclosures of which are hereby incorporated by reference in their entireties), umbilical cord stem cells, amniotic fluid stem cells, amnion derived adherent cells (AMDACs), osteogenic placental adherent cells (OPACs; e.g., the cells described in U.S. Application Publication No. 2010/0047214, the disclosure of which is hereby incorporated by reference in its entirety), adipose stem cells, limbal stem cells, dental pulp stem cells, myoblasts, endothelial progenitor cells, neuronal stem cells, exfoliated teeth derived stem cells, hair follicle stem cells, dermal stem cells, parthenogenically derived stem cells, reprogrammed stem cells, amnion derived adherent cells, or side population stem cells. In other specific embodiments, the non-tumor cells are isolated hematopoietic stem cells or hematopoietic progenitor cells. In other specific embodiments, the non-tumor cells are tissue culture plastic-adherent $CD34^-$, $CD10^+$, $CD105^+$, and $CD200^+$ placental stem cells, e.g., the placental stem cells described in U.S. Pat. No. 7,468,276 and U.S. Pat. No. 8,057,788, the disclosures of which are hereby incorporated by reference in their entireties. In a specific embodiment, said placental stem cells are additionally one or more of $CD45^-$, $CD80^-$, $CD86^-$, or $CD90^+$. In a more specific embodiment, said placental stem cells are additionally $CD45^-$, $CD80^-$, $CD86^-$, and $CD90^+$. Such placental stem cells, in certain embodiments, are immunomodulatory. See, e.g., U.S. Pat. No. 7,682,803 and US 2008/0226595, the disclosures of which are hereby incorporated by reference in their entireties.

In various other specific embodiments, the non-tumor cells are, differentiated cells, e.g., one or more of endothelial cells, epithelial cells, dermal cells, endodermal cells, mesodermal cells, fibroblasts, osteocytes, chondrocytes, natural killer cells, dendritic cells, hepatic cells, pancreatic cells, or stromal cells. In various more specific embodiments, said differentiated cells are, or comprise salivary gland mucous cells, salivary gland serous cells, von Ebner's gland cells, mammary gland cells, lacrimal gland cells, ceruminous gland cells, eccrine sweat gland dark cells, eccrine sweat gland clear cells, apocrine sweat gland cells, gland of Moll cells, sebaceous gland cells. bowman's gland cells, Brunner's gland cells, seminal vesicle cells, prostate gland cells, bulbourethral gland cells, Bartholin's gland cells, gland of Littre cells, uterus endometrium cells, isolated goblet cells, stomach lining mucous cells, gastric gland zymogenic cells, gastric gland oxyntic cells, pancreatic acinar cells, paneth cells, type II pneumocytes, clara cells, somatotropes, lactotropes, thyrotropes, gonadotropes, corticotropes, intermediate pituitary cells, magnocellular neurosecretory cells, gut cells, respiratory tract cells, thyroid epithelial cells, parafollicular cells, parathyroid gland cells, parathyroid chief cell, oxyphil cell, adrenal gland cells, chromaffin cells, Leydig cells, theca interna cells, corpus luteum cells, granulosa lutein cells, theca lutein cells, juxtaglomerular cell, macula densa cells, peripolar cells, mesangial cell, blood vessel and lymphatic vascular endothelial fenestrated cells, blood vessel and lymphatic vascular endothelial continuous cells, blood vessel and lymphatic vascular endothelial splenic cells, synovial cells, serosal cell (lining peritoneal, pleural, and pericardial cavities), squamous cells, columnar cells, dark cells, vestibular membrane cell (lining endolymphatic space of ear), stria vascularis basal cells, stria vascularis marginal cell (lining endolymphatic space of ear), cells of Claudius, cells of Boettcher, choroid plexus cells, pia-arachnoid squamous cells, pigmented ciliary epithelium cells, nonpigmented ciliary epithelium cells, corneal endothelial cells, peg cells, respiratory tract ciliated cells, oviduct ciliated cell, uterine endometrial ciliated cells, rete testis ciliated cells, ductulus efferens ciliated cells, ciliated ependymal cells, epidermal keratinocytes, epidermal basal cells, keratinocyte of fingernails and toenails, nail bed basal cells, medullary hair shaft cells, cortical hair shaft cells, cuticular hair shaft cells, cuticular hair root sheath cells, hair root sheath cells of Huxley's layer, hair root sheath cells of Henle's layer, external hair root sheath cells, hair matrix cells, surface epithelial cells of stratified squamous epithelium, basal cell of epithelia, urinary epithelium cells, auditory inner hair cells of organ of Corti, auditory outer hair cells of organ of Corti, basal cells of olfactory epithelium, cold-sensitive primary sensory neurons, heat-sensitive primary sensory neurons, Merkel cells of epidermis, olfactory receptor neurons, pain-sensitive primary sensory neurons, photoreceptor rod cells, photoreceptor blue-sensitive cone cells, photoreceptor green-sensitive cone cells, photoreceptor red-sensitive cone cells, proprioceptive primary sensory neurons, touch-sensitive primary sensory neurons, type I carotid body cells, type II carotid body cell (blood pH sensor), type I hair cell of vestibular apparatus of ear (acceleration and gravity), type II hair cells of vestibular apparatus of ear, type I taste bud cells, cholinergic neural cells, adrenergic neural cells, peptidergic neural cells, inner pillar cells of organ of Corti, outer pillar cells of organ of Corti, inner phalangeal cells of organ of Corti, outer phalangeal cells of organ of Corti, border cells of organ of Corti, Hensen cells of organ of Corti, vestibular apparatus supporting cells, taste bud supporting cells, olfactory epithelium supporting cells, Schwann cells, satellite cells, enteric glial cells, astrocytes, neurons, oligodendrocytes, spindle neurons, anterior lens epithelial cells, crystallin-containing lens fiber cells, hepatocytes, adipocytes, white fat cells, brown fat cells, liver lipocytes, kidney glomerulus parietal cells, kidney glomerulus podocytes, kidney proximal tubule brush border cells, loop of Henle thin segment cells, kidney distal tubule cells, kidney collecting duct cells, type I pneumocytes, pancreatic duct cells, nonstriated duct cells, duct cells, intestinal brush border cells, exocrine gland striated duct cells, gall bladder epithelial cells, ductulus efferens nonciliated cells, epidymal principal cells, epidymal basal cells, ameloblast epithelial cells, planum semilunatum epithelial cells, organ of Corti interdental epithelial cells, loose connective tissue fibroblasts, corneal keratocytes, tendon fibroblasts, bone marrow reticular tissue fibroblasts, nonepithelial fibroblasts, pericytes, nucleus pulposus cells, cementoblast/cementocytes, odontoblasts, odontocytes, hyaline cartilage chondrocytes, fibrocartilage chondrocytes, elastic cartilage chondrocytes, osteoblasts, osteocytes, osteoclasts, osteoprogenitor cells, hyalocytes, stellate cells (ear), hepatic stellate cells (Ito cells), pancreatic stelle cells, red skeletal muscle cells, white skeletal muscle cells, intermediate skeletal muscle cells, nuclear bag cells of muscle spindle, nuclear chain cells of muscle spindle, satellite cells, ordinary heart muscle cells, nodal heart muscle cells, Purkinje fiber cells, smooth muscle cells, myoepithelial cells of iris, myoepithelial cell of exocrine glands, reticulocytes, megakaryocytes, monocytes, connective tissue macrophages. epidermal Langerhans cells, dendritic cells, microglial cells, neutrophils, eosinophils, basophils, mast cell, helper T cells, suppressor T cells, cytotoxic T cell, natural Killer T cells, B cells, natural killer cells, melanocytes, retinal pigmented epithelial cells, oogonia/oocytes, spermatids, spermatocytes, spermatogonium cells, spermatozoa, ovarian follicle cells, Sertoli cells, thymus epithelial cell, and/or interstitial kidney cells.

In certain embodiments, the non-tumor cells are primary culture cells, cells that have been directly obtained from a tissue or organ without culturing, cells that have been cultured in vitro, or cells of a cell line, e.g., partially, conditionally, or fully immortalized cells.

Such non-tumor cells may be isolated from the relevant tissue or organs, e.g., from particular glands, using one or more art-known proteases, e.g., collagenase, dispase, trypsin, LIBERASE, or the like. Tissue may be physically dispersed prior to, during, or after treatment of the tissue with a protease, e.g., by dicing, macerating, filtering, or the like. Cells may be cultured using standard, art-known cell culture techniques prior to use in the methods described herein, e.g., in order to produce homogeneous or substantially homogeneous cell populations, to select for particular cell types, or the like.

Isolation, culture, and identification of pituitary gland cells may be performed according to procedures known in the art, e.g., using lipocortin 1 (LC1) as a marker according to the procedures disclosed in Christian et al., "Characterization and localization of lipocortin 1-binding sites on rat anterior pituitary cells by fluorescence-activated cell analysis/sorting and electron microscopy," *Endocrinology* 138 (12):5341-5351 (1997); see also Kim et al., "Isolation, culture and cell-type identification of adult human pituitary cells," *Acta Neuropathol.* 68(3):205-208 (1985); Baranowska et al., "Direct effect of cortistatin on GH release from cultured pituitary cells in the rat," *Neuro Endocrinol Lett.* 27(1-2):153-156 (2006).

Isolation, culture, and identification of thyroid gland cells may be performed according to procedures known in the art. See, e.g., Pavlov et al., "Isolation of cells for cytological and cytogenetic studies of the thyroid epithelium," *Morfologiia* 130(6):81-83 (2006); Fayet et al., "Isolation of a normal human thyroid cell line: hormonal requirement for thyroglobulin regulation," *Thyroid* 12(7):539-546 (2002).

Isolation, culture, and identification of adrenal gland cells may be performed according to procedures known in the art. See, e.g., Creutz, "Isolation of chromaffin granules," *Curr Protoc Cell Biol.* Chapter 3:Unit 3.39.1-10 (September 2010); Caroccia et al., "Isolation of human adrenocortical aldosterone-producing cells by a novel immunomagnetic beads method," *Endocrinology* 151(3):1375-80 (2010); Fawcett et al., "Isolation and properties in culture of human adrenal capillary endothelial cells," *Biochem Biophys Res Commun.* 174(2):903-8 (1991); Notter et al., "Rodent and primate adrenal medullary cells in vitro: phenotypic plasticity in response to coculture with C6 glioma cells or NGF," *Exp Brain Res.* 76(1):38-46 (1989).

In certain embodiments, the non-tumor cells produce a biologically-relevant protein or polypeptide. In certain embodiments, said protein or polypeptide is a cytokine or a peptide comprising an active part thereof. In more specific embodiments, said cytokine is adrenomedullin (AM), angiopoietin (Ang), bone morphogenetic protein (BMP), brain-derived neurotrophic factor (BDNF), epidermal growth factor (EGF), erythropoietin (Epo), fibroblast growth factor (FGF), glial cell line-derived neurotrophic factor (GNDF), granulocyte colony stimulating factor (G-CSF), granulocyte-macrophage colony stimulating factor (GM-CSF), growth differentiation factor (GDF-9), hepatocyte growth factor (HGF), hepatoma derived growth factor (HDGF), insulin-like growth factor (IGF), migration-stimulating factor, myostatin (GDF-8), myelomonocytic growth factor (MGF), nerve growth factor (NGF), placental growth factor (P1GF), platelet-derived growth factor (PDGF), thrombopoietin (Tpo), transforming growth factor alpha (TGF-α), TGF-β, tumor necrosis factor alpha (TNF-α), vascular endothelial growth factor (VEGF), or a Wnt protein.

In other specific embodiments, said protein or polypeptide is a soluble receptor for AM, Ang, BMP, BDNF, EGF, Epo, FGF, GNDF, G-CSF, GM-CSF, GDF-9, HGF, HDGF, IGF, migration-stimulating factor, GDF-8, MGF, NGF, P1GF, PDGF, Tpo, TGF-α, TGF-β, TNF-α, VEGF, or a Wnt protein.

In other specific embodiments, said protein or polypeptide is an interleukin, e.g., interleukin-1 alpha (IL-1α), IL-1β, IL-1F1, IL-1F2, IL-1F3, IL-1F4, IL-1F5, IL-1F6, IL-1F7, IL-1F8, IL-1F9, IL-2, IL-3, IL-4, IL-5, IL-6, IL-7, IL-8, IL-9, IL-10, IL-11, IL-12 35 kDa alpha subunit, IL-12 40 kDa beta subunit, both IL-12 alpha and beta subunits, IL-13, IL-14, IL-15, IL-16, IL-17A, IL-17B, IL-17C, IL-17D, IL-17E, IL-17F isoform 1, IL-17F isoform 2, IL-18, IL-19, IL-20, IL-21, IL-22, IL-23 p19 subunit, IL-23 p40 subunit, IL-23 p19 subunit and IL-23 p40 subunit together, IL-24, IL-25, IL-26, IL-27B, IL-27-p28, IL-27B and IL-27-p28 together, IL-28A, IL-28B, IL-29, IL-30, IL-31, IL-32, IL-33, IL-34, IL-35, IL-36α, IL-36β, IL-36γ.

In other specific embodiments, said protein or polypeptide is a soluble receptor for IL-1α, IL-1β, IL-1F1, IL-1F2, IL-1F3, IL-1F4, IL-1F5, IL-1F6, IL-1F7, IL-1F8, IL-1F9, IL-2, IL-3, IL-4, IL-5, IL-6, IL-7, IL-8, IL-9, IL-10, IL-11, IL-12 35 kDa alpha subunit, IL-12 40 kDa beta subunit, IL-13, IL-14, IL-15, IL-16, IL-17A, IL-17B, IL-17C, IL-17D, IL-17E, IL-17F isoform 1, IL-17F isoform 2, IL-18, IL-19, IL-20, IL-21, IL-22, IL-23 p19 subunit, IL-23 p40 subunit, IL-24, IL-25, IL-26, IL-27B, IL-27-p28, IL-28A, IL-28B, IL-29, IL-30, IL-31, IL-32, IL-33, IL-34, IL-35, IL-36α, IL-36β, IL-36γ.

In other specific embodiments, said protein or polypeptide is an interferon (IFN), e.g., IFN-α, IFN-β, IFN-γ, IFN-λ1, IFN-λ2, IFN-λ3, IFN-K, IFN-ε, IFN-κ, IFN-τ, IFN-δ, IFN-ζ, IFN-ω, or IFN-ν.

In other specific embodiments, said protein or polypeptide is a soluble receptor for IFN-α, IFN-β, IFN-γ, IFN-λ1, IFN-λ2, IFN-λ3, IFN-K, IFN-ε, IFN-κ, IFN-τ, IFN-δ, IFN-ζ, IFN-ω, or IFN-ν.

In other specific embodiments, said protein or polypeptide is insulin or proinsulin. In other specific embodiments, said protein is a receptor for insulin. In a more specific embodiment, said cells produce one or more of prohormone convertase 1, prohormone convertase 2, or carboxypeptidase E.

In another specific embodiment, said protein or polypeptide is leptin (LEP).

In other specific embodiments, said protein is erythropoietin (Epo).

In another specific embodiment, said protein is thrombopoietin (Tpo).

The non-tumor cells, in certain embodiments, comprise cells that produce dopamine, or a precursor to dopamine. In a specific embodiment, said protein is tyrosine 3-monooxygenase. In a more specific embodiment, said cells express aromatic L-amino acid decarboxylase.

In another specific embodiment, said protein or polypeptide is a hormone or prohormone. In more specific embodiments, said hormone is antimullerian hormone (AMH), adiponectin (Acrp30), adrenocorticotropic hormone (ACTH), angiotensin (AGT), angiotensinogen (AGT), antidiuretic hormone (ADH), vasopressin, atrial-natriuretic peptide (ANP), calcitonin (CT), cholecystokinin (CCK), corticotrophin-releasing hormone (CRH), erythropoietin (Epo), follicle-stimulating hormone (FSH), testosterone, estrogen, gastrin (GRP), ghrelin, glucagon (GCG), gonadotropin-releasing hormone (GnRH), growth hormone (GH), growth hormone releasing hormone (GHRH), human chorionic gonadotropin (hCG), human placental lactogen (HPL), inhibin, leutinizing hormone (LH), melanocyte stimulating hormone (MSH), orexin, oxytocin (OXT), parathyroid hormone (PTH), prolactin (PRL), relaxin (RLN), secretin (SCT), somatostatin (SRIF), thrombopoietin (Tpo), thyroid-stimulating hormone (Tsh), and/or thyrotropin-releasing hormone (TRH).

In another specific embodiment, said protein or polypeptide is cytochrome P450 side chain cleavage enzyme (P450SCC).

In other specific embodiments, said protein is a protein missing or malfunctioning in an individual who has a genetic disorder or disease. In specific embodiments, said genetic disease is familial hypercholesterolemia and said protein is low density lipoprotein receptor (LDLR); said genetic disease is polycystic kidney disease, and said protein is polycystin-1 (PKD1), PKD-2 or PKD3; or said genetic disease is phenylketonuria and said protein is phenylalanine hydroxylase.

5. EXAMPLES

5.1. Example 1

Conductivity of Decellularized Placental Vasculature

This Example demonstrates a method of efficiently and gently decellularizing placenta in such a manner as to preserve the vascular matrix of the placenta substantially intact, and the successful repopulation of the vascular matrix with non-placental cells.

Materials and Methods

Placentas: All placentas used were pre-perfused to remove placental and umbilical cord blood. The perfusion tubing in the two umbilical cord arteries were kept and used for perfusion decellularization. Placentas were either used for perfusion decellularization immediately or frozen in −80° C. freezer in a sealed plastic package.

Perfusion Decellularization: Decellularization solutions comprising phosphate-buffered saline (PBS) and 1% Triton X-100, 0.5% SDS, and PBS, respectively, were sequentially infused into the placenta via the arteries of the umbilical cord. Residual detergent following decellularization was rinsed off using a PBS solution. Progress of decellularization was monitored by visual inspection for the morphology changes of the placenta, by analysis of DNA content, and by H&E staining of the decellularized tissues.

Perfusion decellularization was set up using a peristaltic pump (VWR) with controlled flow rate between 8 to 16 mL/min, with a second, linked peristaltic pump to drain the flow-through of solution into a waste bin. Each step of perfusion utilized approximately 10 to 20 L of medium over the course of between 8 and 24 hrs. After completing the last PBS perfusion, the decellularized placental vascular scaffold was preserved in PBS with antibiotics (1% penicillin+ streptomycin) at 4° C. in, e.g., a stainless pan or desiccator (VWR). In a modification of the protocol, placentas were frozen at −80° C. for more than 24 hrs and thawed at room temperature for 24 hours before decellularization as above.

DNA Content Analysis: The DNA content in the placental tissues was assessed by extracting and measuring DNA amount of the tissues during the processing, expressed as μg DNA/mg wet tissue weight) using a Tissue DNA isolation kit (OMEGA Bio-Tek, Cat#D3396-01). For each processing step, 4 to 6 different individual samples were used to extract DNA.

Perfusion Solutions: Stock solutions of 10% Triton X-100, 20% SDS, and 10×PBS were purchased from AMRESCO, VWR, or Sigma and diluted with distilled water to desired concentrations.

Fluid conductivity: A surface vessel fluid conductivity (SVFC) assay was established to access fluid conductivity of decellularized placental vascular scaffold. Briefly, a 0.4% Trypan Blue (100 mL to 200 mL) solution was infused into the two arteries of the umbilical cord. Distance of the dye on the location of the placental disc and the radius of the placental disc were measured. The conductivity is determined by the distance of dye travelled (D) and the radius of the placental disc (R) at the same position and calculated as the following formula (D/R)×100%. For each placenta, 8 different data points were collected and the average is taken.

Cell conductivity: The cell conductivity of the decellularized placenta vascular scaffold was investigated by the distribution of luciferase expressing cells after infusion of luciferase labeled cells. The distribution of cells was imaged using a Xenogen IVIS Spectrum, and digital bioluminescent data was analyzed with Living Image 3.0 software.

Results

Perfusion Decellularization: Method Development

Upon perfusion decellularization, as outlined above, the decellularized vascular tree showed a translucent or transparent appearance, indicating substantially complete decellularization. This translucent or transparent appearance was reproducible across several different placentas, and was not altered by freezing the placenta, or not, prior to decellularization.

We simplified the decellularization method by using two steps of detergent-perfusion (1% Triton X-100 followed by 0.5% SDS) instead of multiple steps and multiple detergents as described above. Morphology inspection (decellularized human placenta appeared as a white and opaque tissue from top to the bottom of the placenta disc). DNA content analysis confirmed that such simplified two-step method can efficiently and sufficient to achieve significant DNA reduction and decellularization.

Characterization of Decellularized Placental Vascular Scaffold: DNA Content Analysis DNA content of the tissues was used to examine the extent of decellularization of five experimental placentas. It was shown that first Triton X-100 perfusion significantly increased the DNA content in the tissue as compared to placental tissue not treated with Triton X-100 (P=0.02), possibly because Triton X-100 improved recovery of DNA from tissues. Subsequent 0.5% SDS perfusion reduced the average total DNA content by 69% (N=5, ranges from 81% to 50%) significantly different as comparing with the Triton X-100 treatment step (p=0.01). The second cycle of Triton X-100 and SDS perfusion appeared to increase the DNA content, probably by further releasing out more DNA from tissues. The final wash of PBS also reduced the amount of DNA in the placental tissue. DAPI and H&E staining confirmed that, after two rounds of perfusion decellularization, few intact nuclei remained in the decellularized placenta matrix. Residual DNA was most likely genomic DNA released during decellularization, which is removable using, e.g., DNAseI treatment. It is worth noting that the residual DNA is present in the decellularized matrix, and not in the vascular system, since isolated vessels from the decellularized placenta matrix have little DNA content.

Characterization of Decellularized Placental Vascular Scaffold: Fluid Conductivity To demonstrate the intactness of the placental vascular system after decellularization, Trypan Blue dye was infused into the vascular system after decellularization. Trypan blue dye was distributed from the center of the vein to the edge of the placenta disc, indicating that both the major and small vascular system retained conductivity post-decellularization. To quantitatively characterize the fluid conductivity, a method called "surface vessel fluid conductivity" (SVFC) was established as described under "Methods" above. SVFC of each placenta after Trypan blue dye infusion was measured at eight positions around the placenta, radially dividing the placenta into roughly equal portions. The average surface vessel fluid conductivity of three placentas was determined to be 93%.

Characterization of Decellularized Placental Vascular Scaffold: Cell Conductivity and Distribution To investigate the cell conductivity of the decellularized human placental vascular scaffold, luciferase labeled cells were perfused into the decellularized placental vasculature, and the distribution of the cells within the decellularized matrix was determined by luminescence imaging and digital analysis. Four individual experiments were performed (Study 1 to Study 4).

Study 1 was a feasibility study directed to method establishment using 300 million 4T1-luc mouse breast carcinoma cells as the infused cell population. Placentas were frozen at −80° C. overnight, and thawed. The placentas were decellularized using 0.1×PBS. Before cell infusion, the placenta is pre-conditioned by perfusing 500 mL of 5% FCS-PBS. Cells resuspended in 300 mL cell culture medium were infused first, followed by an infusion of luciferin at 1.2 mg/mL. Images were taken at three different settings and at 0 hr and 2 hr after cell infusion. Quantitative image analysis was performed (circular zone and pie zone) for cell distribution. The results showed that Luciferase-labeled cells infused into placental scaffold could be imaged and visualized in this novel study method. Cells were found to be distributed in both major and small vessels throughout most of the placental vasculature.

Study 2 confirmed the results of study 1 by using detergent-decellularization derived human placental vascular scaffold. In particular, the effects of any residual detergent on Luciferase activity and cell distribution signals was evaluated using 300 million 4T1-luc mouse breast carcinoma cells as the infused cell population. Decellularization was performed by freezing and thawing, as described above, followed by decellularization with two rounds of sequential decellularization using 1% Triton X-100 and 0.5% SDS, followed by a PBS wash. Placenta matrix was also pre-conditioned with 5% FCS in PBS before cell infusion. In this study, the cells and Luciferin were premixed together and infused. Confirming the results of Study 1, the luciferase activity of cells remained at 2 hrs after infusion, indicating that detergent-based decellularization of placental scaffold has no toxicity for cells.

Study 3 was designed to demonstrate the distribution of human cells in the decellularized placental vascular scaffold. In contrast to Study 1 and Study 2, 300 million human breast carcinoma MDA-231-Luc cells, resuspended in 300 mL of growth medium, were infused into a decellularized placenta, prepared as in Study 1 and Study 2. The human cells distributed throughout the placental vasculature as efficiently as did the mouse cells.

Study 4 was designed to demonstrate decellularized human placental vascular scaffold can be used to culture cells for tissue engineering by cell repopulation. A prototype bioreactor system was set up by culturing intact placental vasculature matrix in a sterile stainless pan (9×2 inches). Circulation through the matrix was established using by insertion of input tubing into the two cord artery matrices, and insertion of output tubing into the placental vein matrix to collect flow-through medium/cells. The placenta was cultured in 37° C. incubator during perfusion of the cells. Circulation was maintained by a peristaltic pump with controlled flow rate about 6 to 12 mL/min. 200 million human breast carcinoma MDA-231-Luc cells were resuspended in 500 mL of growth medium, and were continuously infused/reinfused into decellularized human placental vasculature using the system described as above. Circulation was maintained overnight, after which culture was discontinued and the placental vasculature was infused with Luciferin as in Studies 1-3.

After incubation overnight in this system, there was no contamination in the culture. Analysis of the flow through medium in the pan found no cells, suggesting that substantially all of the infused cells were retained in the placental vascular scaffold, likely due to the repeated circulation. The imaging analysis revealed that the cell distribution in the vascular system is similar as previous studies. There is improvement in the even distribution as shown in the pie-analysis. Strong signals also found on the maternal face of the placenta, demonstrating that the cells were distributed throughout the thickness of the placenta, from the fetal face of the placenta (that is, the side with the umbilical cord) to the maternal face (that is, the opposite side).

Conclusions

This set of experiments demonstrated a method to decellularize a whole human placenta, while retaining a substantially intact vascular scaffold, and that the vascular scaffold can conduct fluid efficiently with minimal loss. These results also indicate that placental scaffold can be repopulated and used in the methods presented herein.

5.2. Example 2

Cell Culture Using Decellularized Placental Vascular Scaffold

This Example demonstrates that additional human cell types can be infused into, and cultured within, decellularized placental vascular scaffold.

Materials and Methods

Human decellularized placenta scaffolds, prepared as described in Example 1, above, were used in this study.

Placental scaffold sterilization: Decellularized placenta scaffold was sterilized in 0.1% peracetic acid (PAA) in PBS for 3 hours, with solution change every 1 hr, at room temperature. Agitation washes 6 times in same amount of PBS for one hour of each change.

Placental scaffold preparation: The decellularized placenta tissue was cut into ~2 to 3 cubic mm micro blocks with surgical blade in sterile condition. The blocks were rinsed with cell culture medium.

Cells for recellularization in culture: PDAC™ expressing green fluorescent protein (GFP-PDAC), human umbilical vein endothelial cells (HUVEC), 293/GFP cells (Cell Biolabs, Inc.), and HepaRG cells were used in the recellularization study. 293/GFP cells are a permanent cell line established from primary embryonic human kidney transformed with human adenovirus type 5 DNA, engineered to stably express green fluorescent protein.

Quantum dot labeling of placenta-derived adherent cells (PDAC™): Quantum dots (QDs) are fluorescent semiconductor nanoparticles, recently adopted for use in in vitro and in vivo bioimaging. In this study, Q605 quantum dots (Invitrogen) was used for labeling PDAC according to vendor's protocol.

Cell growth assay: Growth of cells was determined using an assay based on Promega MTS protocol using CellTiter 96® AQueous Assay kit. In brief, 200 of MTS solution were added into each well of a 96 well assay plate containing 1000 of cells in culture medium per well. The plate was incubated for 1 hour at 37° C. in a humidified, 5% $CO_2$ atmosphere, followed by recordation of absorbance at 490 nm using an ELISA plate reader.

GFP quantitative assay: 293/GFP cells were seeded on the decellularized placental vascular scaffold (~2×2×2 $mm^3$) at $2×10^4$ per 96-well. Cell attachment was measured in a quantitative GFP ELISA assay with a GFP ELISA Kit (AKR-121) (Cell Biolabs, Inc.) according to vendor's protocol.

Live/dead cell determination: Live and dead cells were determined by CytoSelect 96-well Anoikis Assay staining kit (CBA-081) (Cell Biolabs, Inc.).

Histology evaluation: The histology evaluation of decellularization and recellularization were performed with H& E staining, and Masson Trichrome staining (Histoserv). The tissue sections were analyzed and recorded under microscope.

Hepatocyte functional assays: Hepatocyte functions were determined by albumin production (Albumin Blue Fluorescent Assay Kit; Active Motif, Carlsbad, Calif.); urea assay (Quantichrom Urea Assay NC9283832 Bioassay Systems No. DIUR-500, Fisher Scientific Co.); and P450assay (P450-Glo™ CYP3A4 Assay (Luciferin-PFBE) Cell-Based/Biochemical Assay, Promega)

Results:

Decellularized Human Placental Vascular Scaffold (DH-PVS) Maintains Architecture and ECM Components Decellularized placenta presents as transparent tissue with micro vascular tree extension, which has rich cotton like matrix.

To determine the effect of the decellularization process on placental morphology and architecture, the decellularized vascular scaffold was fixed in 4% paraformaldehyde and sectioned for histology analysis after hematoxylin and eosin stain (H & E). Decellularization removed substantially all cells, as evidenced by the lack of hematoxylin staining of cell nuclei. Placental structures readily visible under microscope after H&E staining include large vessels surrounded by villous tissue, and the characteristic spongy matrix of the placenta, the smallest branches of the chorionic villi. In contrast to the images of after decellularization, nondecellularized control placenta tissue showed a rich cell distribution with positive stained of blue cell nuclear for hematoxylin.

To assess whether decellularization process had an adverse effect on extracellular matrix (ECM) components and arrangement, the same tissue block of decellularized placenta were fixed and stained by H&E or Masson's trichrome. Visual inspection under microscopy revealed that the decellularized placenta tissue was indeed acellular and that the placenta matrix was intact. Matrix structure and collagen (ECM) (green color by Masson's staining) remained.

Decellularized Human Placental Vascular Scaffold (DHPVS) can be Recellularized with Cells in Culture To determine whether decellularized placenta scaffold could support cell growth in culture, PDAC™ and human umbilical vein endothelial cells (HUVECs) were seeded over a block of DHPVS, and injected into the block, and cultured at 37° C. in a humidified, 5% CO2 atmosphere for 14 days. The resulting DHPVS tissue blocks were sectioned and stained by H&E for recellularization analysis. Visual inspection under microscopy revealed that PDAC™ could grow along the decellularized scaffold surface, and maintain in live morphology in the scaffold space, and that HUVECs has repopulated at least a portion of the vascular scaffold.

Quantitative Evaluation of Cell Attachment and Growth on Decellularized Human Placental Vascular Scaffold (DHPVS)

To assess cell attachment on DHPVS in culture, this study used a green fluorescent protein (GFP) quantization assay as most of imaging studies of GFP labeled cells are qualitative. Current ELISA based assays allow detection of as little as 30 pg/ml of GFP in the culture. 293/GFP cells seeded onto DHPVS showed ~1.4 fold (p=0.004) better growth, by ELISA, than growth of the same cells in 96-well along after 24 h.

PDAC™ can Adhere and Proliferate on Decellularized Human Placental Vascular Scaffold (DHPVS)

To determine whether DHPVS is capable of supporting growth of cells, PDAC™-GFP cells were seeded onto DHPVS blocks and cultured. The cells proliferated during culture, and were well integrated into DHPVS for growth, as visualized by fluorescent imaging. Proliferation of PDAC™-GFP cells in DHPVS was also demonstrated by an MTS assay. PDAC™-GFP was seeded onto DHPVS blocks (~2×2×2 mm$^3$) at 2×10$^4$ per 96-well in growth medium. The scaffolds were moved on day 1 and day 3 to new 96-well for MTS assay to assess cell proliferation. Results indicated that DHPVS is a suitable scaffold for PDAC™ adherence and proliferation.

PDAC™-GFP Adhere and Grow on Decellularized Placental Vessels

To assess PDAC™ attachment and growth on isolated placental decellularized vessels, decellularized umbilical cord (~2 mm thickness), including vessels, was seeded with PDAC™-GFP (0.5×10$^6$ in 2 ml medium) and cultured for 3 days, and visualized as described in Methods, above. The resulting fluorescent image showed that PDAC™-GFP cells preferentially adhere to and grow around decellularized vessels.

As an additional approach to assess cell attachment and growth in decellularized placental small vessels, PDAC™-GFP cells and Q605 labeled PDAC™ were equally mixed to a total of 1×10$^6$/mL and injected into small vessels within the DHPVM and cultured at 37° C. in growth medium for 3 days. Photographs were taken for the two cell populations in the same vessel area under fluorescent microscope. Representative fluorescent images of both GFP-expressing cells and Qdot-labeled cells show that PDAC™ can attach and grow inside decellularized placental small vessels.

Cell attachment and growth of tissue specific cell were also demonstrated in decellularized placental micro-vessels. To achieve this goal, 300 μl of 293/GFP cells at a concentration of 1×10$^6$/mL were infused into a DHPVM block (~3×3×5 mm$^3$) and cultured in 24-well plate. After 7 days, the cells were visualized and photographed. Results demonstrated that 293/GFP cells can grow readily, and are well-distributed in DHPVS over the course of the 7 days.

Hepatocytes can Maintain Functional Growth in Decellularized Human Placental Vascular Scaffold To establish hepatocyte growth on DHPVS, HepaRG cells were seeded at 2×10$^4$/96-well over DHPVS, or injected into DHPVS, and cultured in 620 medium. The cells were visualized and photographed on Day 4 and Day 7 under phase contrast microscopy. Results indicated that HepaRG cells displayed an aggregate growth pattern and hepatocyte growth morphology in the presence of DHPVS. Functional analysis of hepatocytes using an albumin secretion assay was performed on culture day 3, day 6, and day 8. The culture medium samples were collected and tested by the Albumin Blue Fluorescent Assay Kit (Active Motif). Standard curves were generated using purified human albumin. Hepatocytes cultured alone were used as a control. Hepatocytes cultured on DHPVS were found to produce significantly more albumin than cells grown in the absence of DHPVS (P<0.02). The results indicate that hepatocytes maintain important functions when cultured in DHPVS.

5.3. Example 3

Drug Testing Using Decellularized Placental Vascular Scaffold

This Example demonstrates that compositions comprising decellularized placental vascular scaffold and cells can be used to test anti-cancer drugs.

Blocks of decellularized placental vascular scaffold (DPVS) in 24-well plates were seeded with HCT116 cells (1×10$^5$ cells/per well), a human colorectal cancer cell line. As a control, HCT116 cells were cultured in wells only, i.e., in the absence of DPVS. Trichostatin A (TSA), a drug contemplated for use in the treatment of cancer, was added to the DPVS/cells or cells alone at concentrations of 20 μM and 100 μM, or was not added at all (as a control). After 48 hours of culture, cell viability was measured by MTS assay. As shown in Table 1, both concentrations of TSA inhibited proliferation of the HCT116 cells alone as well as the HCT116 cells cultured on DPVS, with the latter showing different sensitivity to the drug. Thus, DPVS can be used a platform for assessing cancer cell killing by potential anti-tumor compounds.

TABLE 1

|  | HCT116 | | | HCT116 + DPVS | | |
| --- | --- | --- | --- | --- | --- | --- |
|  | Control | TSA 20 uM | TSA 100 uM | Control | TSA 20 uM | TSA 100 uM |
| Inhibition | 100.00% | 11.21% | 10.36% | 100.00% | 97.00% | 73.32% |

5.4. Example 4

Drug Testing Using Decellularized Placental Vascular Scaffold

This Example demonstrates that compositions comprising decellularized placental vascular scaffold and cells can be used to test anti-cancer drugs.

Cells expressing luciferase were detected visually and quantitatively, using the Xenogen IVIS spectrum, by measuring Luciferase activity of the cells, which is indicative of cell number.

To examine the anti-cancer drug effect on cancer cells grown in DPVS, 1.5×10$^5$ MDA-MB231/Luciferase cells (a human breast cancer (adenocarcinoma) cell line that expresses luciferase; Cell Biolabs) were seeded onto DPVS in 6-well plates. One set of cells/DPVS was treated with Trichostatin A (TSA, 100 ng/mL) for 24 hours. Luciferase expression by the TSA-treated cells cultured on DPVS was compared with control cultures comprising cells/DPVS that were not treated with TSA. The luciferase signals of the TSA-treated wells were much lower than the signals for the untreated cells/DPVS ($8.22 \times 10^6$ vs. $25.63 \times 10^6$, respectively), indicating that TSA treatment resulted in a lower number of total cells. Thus, DPVS can be used to study the ability of cancer drugs, e.g., TSA, to affect cancer cell growth in a three-dimensional context.

5.5. Example 5

Placental Cotyledons can be Used as DPVS for Drug Testing

This example demonstrates that placental cotyledons can be used as platforms for drug testing.

Placental cotyledons were isolated from placenta and decellularized as described above. The average area of a single cotyledon was determined to represent about 10% of a whole placenta. Decellularized placenta cotyledons comprise vasculature and were shown to be able to circulate fluid. The fluid circulation rates (efflux volume/influx volume) of single cotyledons isolated from seven different placentas were evaluated and determined to be, on average, 28.92%. Thus, placental cotyledons represent smaller physical units that can be used as DPVS in accordance with the uses described in the hereinabove.

To demonstrate that isolated single placental cotyledons can be used for evaluating potential antitumor compounds, two types of cancer cells, MDA-MB231/Luc and CRL1803-TT (thyroid tissue carcinoma), were infused into the vasculature of a single isolated cotyledon ($3 \times 10^6$ cells/cotyledon). Trichostatin A (TSA, 100 ng/mL) was added to the growth medium (300 mL) and the cells were cultured for 10 days in a bioreactor. As a control, MDA-MB231/Luc and CRL1803-TT were infused into the vasculature of a single isolated cotyledon ($3 \times 10^6$ cells/cotyledon) and cultured in growth medium only for 10 days in a bioreactor.

Figure 1B:
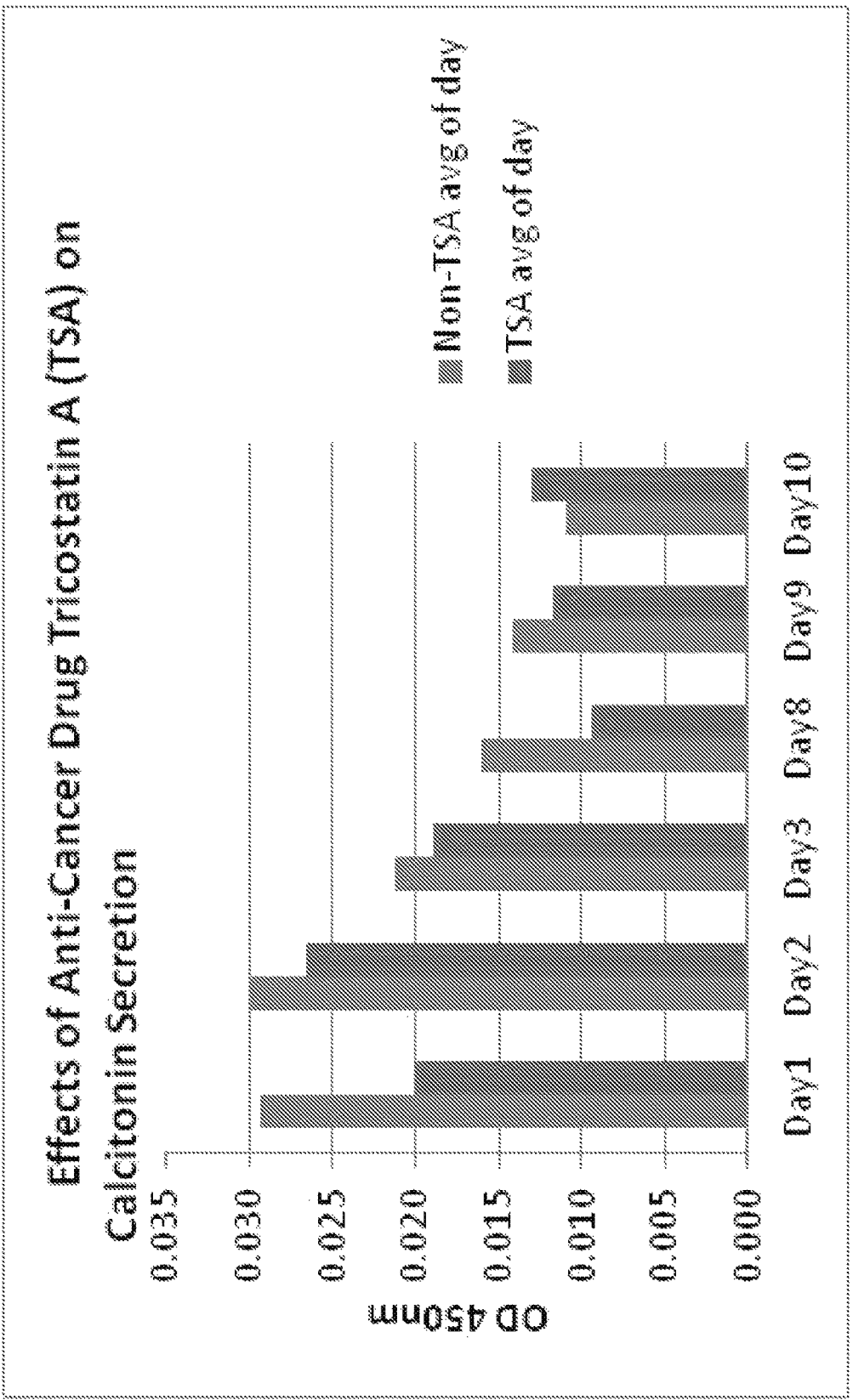
FIG. 1B depicts measured levels of calcitonin secretion by tumor cells grown in placental cotyledons in the presence (leftmost, light colored bars) and absence (rightmost, dark colored bars) of Trichostatin A (TSA) over a 10-day culture period.

Culture medium was collected throughout the culture period and measured for Calcitonin levels by ELISA. In addition, at the end of the culture (day-10), the numbers of viable cells in both the TSA-treated and control cotyledons were determined by MTS assay. As shown in FIG. 1A, TSA-treated cotyledon/cells demonstrated reduced cell survival as compared to the growth medium control. Further, as shown in FIG. 1B, Calcitonin production by the cells was reduced in the TSA-treated cotyledon/cell group. These data further confirm that placental cotyledons can be used for testing anti-tumor drugs.

5.6. Example 6

Drug Testing Using Placental Cotyledons

This Example demonstrates that placental cotyledons can be used to test anti-cancer drugs, as analyzed using the Xenogen IVIS imaging system.

MDA-MB231/Luciferase positive cells were infused into the vasculature of a single isolated cotyledon ($40 \times 10^6$ cells/cotyledon). Trichostatin A (TSA, 100 ng/mL) was added to the growth medium (300 mL) and the cells were cultured for 4 days in a bioreactor. As a control, an equivalent number ($40 \times 10^6$ cells/cotyledon) of MDA-MB231/Luc cells were infused into the vasculature of a single isolated cotyledon and cultured in growth medium only for 4 days in a bioreactor. After 4 days of culture, each cotyledon was transferred to growth medium comprising Luciferin (150 ng/mL) for 10 minutes. Both cotyledons then were analyzed using the IVIS imaging system. The TSA-treated cotyledon demonstrated a marked decrease in luciferase expression as compared to the cotyledon cultured in the absence of TSA, indicating that viability and proliferation of the cells was affected by the cancer therapeutic and confirming that placental cotyledons can be used as a platform for analysis of antitumor drugs.

EQUIVALENTS

The compositions and methods disclosed herein are not to be limited in scope by the specific embodiments described herein. Indeed, various modifications of the compositions and methods in addition to those described will become apparent to those of skill in the art from the foregoing description and accompanying figures. Such modifications are intended to fall within the scope of the appended claims.

Various publications, patents and patent applications are cited herein, the disclosures of which are incorporated by reference in their entireties. contacting said plurality of tumor cells for a period of time with said antitumor compound, and determining whether said antitumor compound is effective against said tumor cells if said antitumor compound over said period of time reduces the number of said tumor cells or reduces the growth rate of said tumor cells.

What is claimed is:

1. A method of determining effectiveness of a potential antitumor compound against a plurality of tumor cells, comprising introducing a plurality of tumor cells to a decellularized placental vascular scaffold or a decellularized placental cotyledon, contacting said plurality of tumor cells for a period of time with said antitumor compound, and determining whether said antitumor compound is effective against said tumor cells if said antitumor compound over said period of time reduces the number of said tumor cells or reduces the growth rate of said tumor cells.

2. The method of claim 1, comprising (i) determining a first number of tumor cells prior to said contacting, and a second number of tumor cells after said contacting, wherein if said first number is larger than said second number, said antitumor compound reduces the number of tumor cells, and said potential antitumor compound is an antitumor compound; or (ii) determining a first number of tumor cells prior to said contacting, and a second number of tumor cells after said contacting; and further determining a control third number of tumor cells at the same time as said second number of tumor cells, wherein said tumor cells in said control have not been contacted with said antitumor compound; wherein if the difference between said second number and said first number is larger than the difference between said third number and said first number, said antitumor compound reduces the growth rate of said tumor cells, and said potential antitumor compound is an antitumor compound.

3. The method of claim 1, wherein said decellularized placental vascular scaffold or decellularized placental cotyledon from previously frozen mammalian placenta.

4. The method of claim 3, wherein said decellularized placental vascular scaffold or decellularized placental cotyledon comprises a substantially intact vasculature.

5. The method of claim 1, wherein said tumor cells are primary tumor cells or are tumor cell line cells.

6. The method of claim 4, wherein said tumor cells are seeded onto or into said decellularized placental vascular scaffold or decellularized placental cotyledon in liquid suspension through said substantially intact vasculature.

7. The method of claim 1, wherein said method additionally comprises passaging culture medium through said decellularized placental vascular scaffold or decellularized placental cotyledon under conditions such that, in the absence of said antitumor compound, said tumor cells proliferate.

8. The method of claim 4, wherein said method additionally comprises passaging culture medium through said decellularized placental vascular scaffold or decellularized placental cotyledon under conditions such that, in the absence of said antitumor compound, said tumor cells proliferate, and wherein said culture medium is passaged through said substantially intact vasculature.

9. The method of claim 1, wherein said method additionally comprises introducing a plurality of non-tumor cells to said decellularized placental vascular scaffold or decellularized placental cotyledon.

10. The method of claim 9, wherein said non-tumor cells are stromal cells.

11. The method of claim 1, comprising labeling said tumor cells with a label.

12. The method of claim 11, wherein said label is a fluorescent label and/or wherein said label is attached to an antibody.

13. The method of claim 1, wherein said tumor cells are labeled with a fluorescent antibody, and wherein (i) if there is a decrease in fluorescence from said fluorescent antibody after said contacting compared to before said contacting, said potential antitumor compound is an antitumor compound; or (ii) if there is a decrease in the rate of increase in fluorescence from said fluorescent antibody over time after said contacting, as compared to a rate of increase in fluorescence from said fluorescent antibody before said contacting, said potential antitumor compound is an antitumor compound.

14. The method of claim 1, wherein a number of tumor cells is determined by determining an amount of an antigen produced by said tumor cells.

15. The method of claim 14, wherein (i) if there is a decrease in said antigen after said contacting compared to before said contacting, said potential antitumor compound is an antitumor compound; or (ii) if there is a decrease in the rate of increase in said antigen produced by said tumor cells as compared to a rate of increase in said antigen produced by said tumor cells before said contacting, said potential antitumor compound is an antitumor compound.

16. The method of claim 1, wherein said tumor cells are genetically modified to express a marker.

17. The method of claim 16, wherein said marker is a fluorescent protein.

18. The method of claim 16, wherein said marker is luciferase.

19. The method of claim 1, wherein said tumor cells are genetically engineered to express a fluorescent protein, and wherein if there is a decrease in fluorescence from said genetically engineered tumor cells after said contacting compared to before said contacting, said potential antitumor compound is an antitumor compound.

20. The method of claim 1, wherein said tumor cells are genetically engineered to express a fluorescent protein, and wherein if there is a decrease in the rate of increase in fluorescence from said genetically engineered tumor cells over time after said contacting, as compared to a rate of increase in fluorescence from said genetically engineered tumor cells before said contacting, said potential antitumor compound is an antitumor compound.

21. The method of claim 1, wherein said decellularized placental vascular scaffold or decellularized placental cotyledon is shaped to fit a container.

* * * * *